US009150930B2

(12) United States Patent
Arnold

(10) Patent No.: US 9,150,930 B2
(45) Date of Patent: Oct. 6, 2015

(54) RAPID DETECTION OF MYCOBACTERIA

(75) Inventor: Catherine Arnold, London (GB)

(73) Assignee: The Secretary of State for Health, London (GB)

( * ) Notice: Subject to any disclaimer, the term of this patent is extended or adjusted under 35 U.S.C. 154(b) by 482 days.

(21) Appl. No.: 12/937,263

(22) PCT Filed: Apr. 9, 2009

(86) PCT No.: PCT/GB2009/050355
§ 371 (c)(1),
(2), (4) Date: Dec. 21, 2010

(87) PCT Pub. No.: WO2009/125228
PCT Pub. Date: Oct. 15, 2009

(65) Prior Publication Data
US 2011/0097725 A1     Apr. 28, 2011

(30) Foreign Application Priority Data

Apr. 9, 2008 (GB) .................................. 0806431.3

(51) Int. Cl.
*C12Q 1/68* (2006.01)
(52) U.S. Cl.
CPC ...................................... *C12Q 1/689* (2013.01)
(58) Field of Classification Search
None
See application file for complete search history.

(56) References Cited

U.S. PATENT DOCUMENTS

2004/0121366 A1*  6/2004  Keim et al. ....................... 435/6
2006/0292574 A1   12/2006  Jou et al.

FOREIGN PATENT DOCUMENTS

WO    WO 2004/009837 A2    1/2004
WO    WO 2009/125228 A1    10/2009

OTHER PUBLICATIONS

Magdalena et al. Journal of Clinical Microbiology (1998) 36(9): 2471-2476.*
Magdalena et al. Journal of Clinical Microbiology (1998) 36(4): 937-943.*
GenBank Accession No. Y13628, *Mycobacterium tuberculosis* senX3, regX3 genes and 3 putative ORF's (2005).*
Lowe et al. Nucleic Acids Research (1990) 18(7): 1757-1761.*
Broccolo et al. Journal of Clinical Microbiology (2003) 41(10): 4565-4572.*
Valasek et al. Advances in Physiology Education (2005) 29: 151-159.*
Olsvik et al. Clinical Microbiology Reviews (1994) 7(1): 43-54.*
Toubaji et al. Cancer Immunology and Immunotherapy (2008) 57: 1413-1420.*
Hildesheim et al. JAMA (2007) 298(7): 743-753.*
Allix, et al., "Utility of Fast Mycobacterial Interspersed Repetitive Unit-Variable Number Tandem Repeat Genotyping in Clinical Mycobacteriological Analysis,"Clinical Infectious Diseases: An Official Publication of the Infectious Diseases Society of America 39(6), Sep. 15, 2004, pp. 783-789.
EMBL Accession No. CS668215, "RNA Interference Mediated Inhibition of Retinoblastoma (RBI) Gene Expression Using Short Interfering Nucleic Acid (siNA)," Jul. 27, 2006, 1 page.
Geneseq Accession No. AGE09307, "VHL Tumor Supressor, CpG island2 DNA Specific Probe, BL SEQ ID: 130," Jul. 12, 2007, 1 page.
Geneseq Accession No. AOF60605, "Rice RNA Amplifying PCR Primer SEQ ID: 89,"Dec. 27, 2007, 1 page.
International Application No. PCT/GB2009/050355, International Search Report dated Sep. 2, 2009, 8 pages.
Kremer, et al., "Discriminatory Power and Reproducibility of Novel DNA Typing Methods for *Mycobacterium tuberculous* Complex Strains," Journal of Clinical Microbiology, 43(11) Nov. 2005, pp. 5628-5638.
Supply, et al., "Automated High-Throughput Genotyping for Study of Global Epidemiology of *Mycobacterium tuberculosis* Based on Mycobacterial Interspersed Repetitive Units," Journal of Clinical Microbiology 39(10), Oct. 2001, pp. 3563 — 3571.
UK IPO Application No. GB0806431.3, Search report Under Section 17, dated Aug. 6, 2008, 6 pages.
Dye et al., "Evolution of Tuberculosis Control and Prospects for Reducing Tuberculosis Incidence, Prevalence, and Deaths Globally", JAMA, Jun. 8, 2005, 293(22), 2767-2775.
Kamerbeek et al., "Simultaneous Detection and Strain Differentiation of *Mycobacteruim tuberculoisis* for Diagnosis and Epidemiology", J. Clin. Microbiol., Apr. 1997, 35(4), 907-914.
Poulet and Cole, "Repeated DNA Sequences in Mycobacteria", Arch Microbiol, Feb. 1995, 163(2), 79-86.
Thierry et al., "Characterization of a *Mycobacterium tuberculosis* Insertion Sequence, IS6110, and It's Application in Diagnosis", J. Clin. Microbiol., Dec. 1990, 28(12), 2668-2673.
Yuen et al., "IS6110 Based Amplityping Assay and RFLP Fingerprinting of Clinical Isolates of *Mycobacterium tuberculosis*", J. Clin. Pathol., Oct. 1995, 48(10), 924-928.
Fleischmann, R.D. et al., "Whole-genome comparison of *Mycobacterium tuberculosis* clinical and laboratory strains." Journal of Bacteriology, Oct. 2002, vol. 184, No. 19, p. 5479-5490.

(Continued)

*Primary Examiner* — Angela M Bertagna
(74) *Attorney, Agent, or Firm* — Baker & Hostetler LLP

(57) ABSTRACT

The invention provides a method for detecting a mycobacterium belonging to the *Mycobacterium tuberculosis* complex (MTBc) in a sample, the method comprising: (a) contacting the sample with a forward oligonucleotide primer and a reverse oligonucleotide primer; wherein the forward primer hybridizes to a target nucleic acid sequence located within a Mycobacterial Interspersed Repetitive Unit (MIRU) repeat element; and wherein the reverse primer hybridizes to a target nucleic acid sequence located within a MIRU repeat element; (b) extending the forward and reverse primers to generate an amplification product; and (c) detecting the amplification product.

34 Claims, 15 Drawing Sheets

(56) References Cited

OTHER PUBLICATIONS

Supply P. et al., "Variable Human Minisatellite-Like Regions in the *Mycobacterium tuberculosis* Genome." Molecular Microbiology, May 2000, vol. 36, No. 3, p. 762-771.

Boondeekhun, H.S. et al., "Detection of *Clostridium difficile* Enterotoxin Gene in Clinical Specimens by the Polymerase Chain Reaction." Journal of Medical Microbiology, May 1993, vol. 38, No. 5, p. 384-387.

Magalhaes, K.G. et al., "Detection of *Lymnaea columella* Infection by *Fasciola hepatica* Through Multiplex-PCR." Memorias Do Instituto Oswaldo Cruz, Jun. 2004, vol. 99, No. 4, p. 421-424.

Wren, B.W. et al., "Nucleotide Sequence of *Clostridium difficile* Toxin a Gene Fragment and Detection of Toxigenic Strains by Polymerase Chain Reaction." FEMS Microbiology Letters, Jun. 15, 1990, vol. 70, No. 1, p. 1-6.

\* cited by examiner

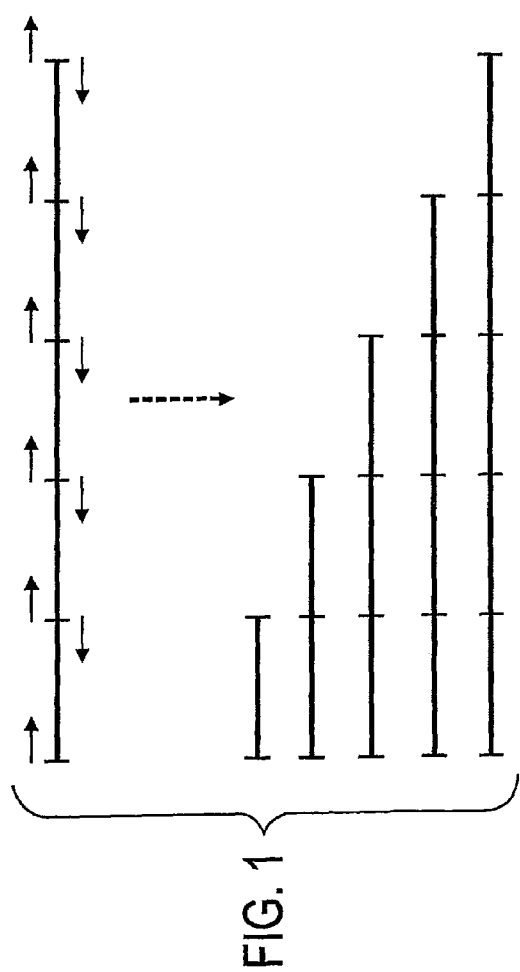
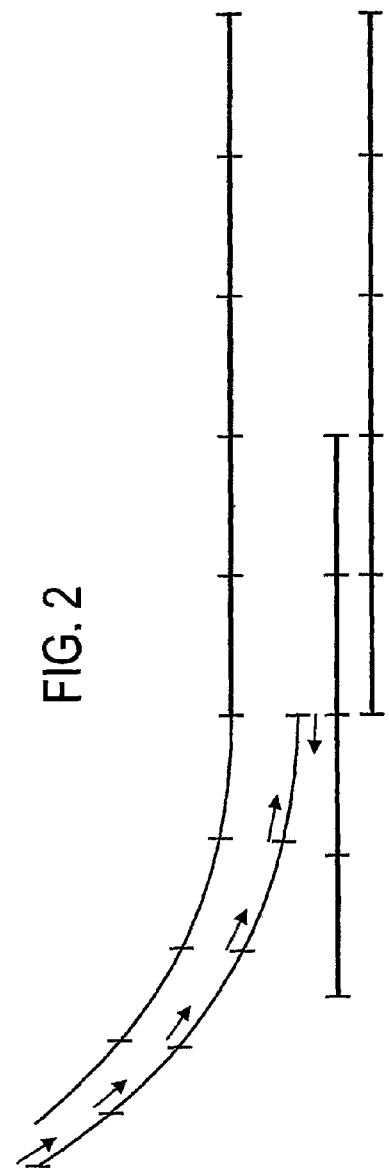

Lane:  1  2  3  4  5  6  7  8  9  10  11

Lane:  1  2  3  4  5  6  7  8

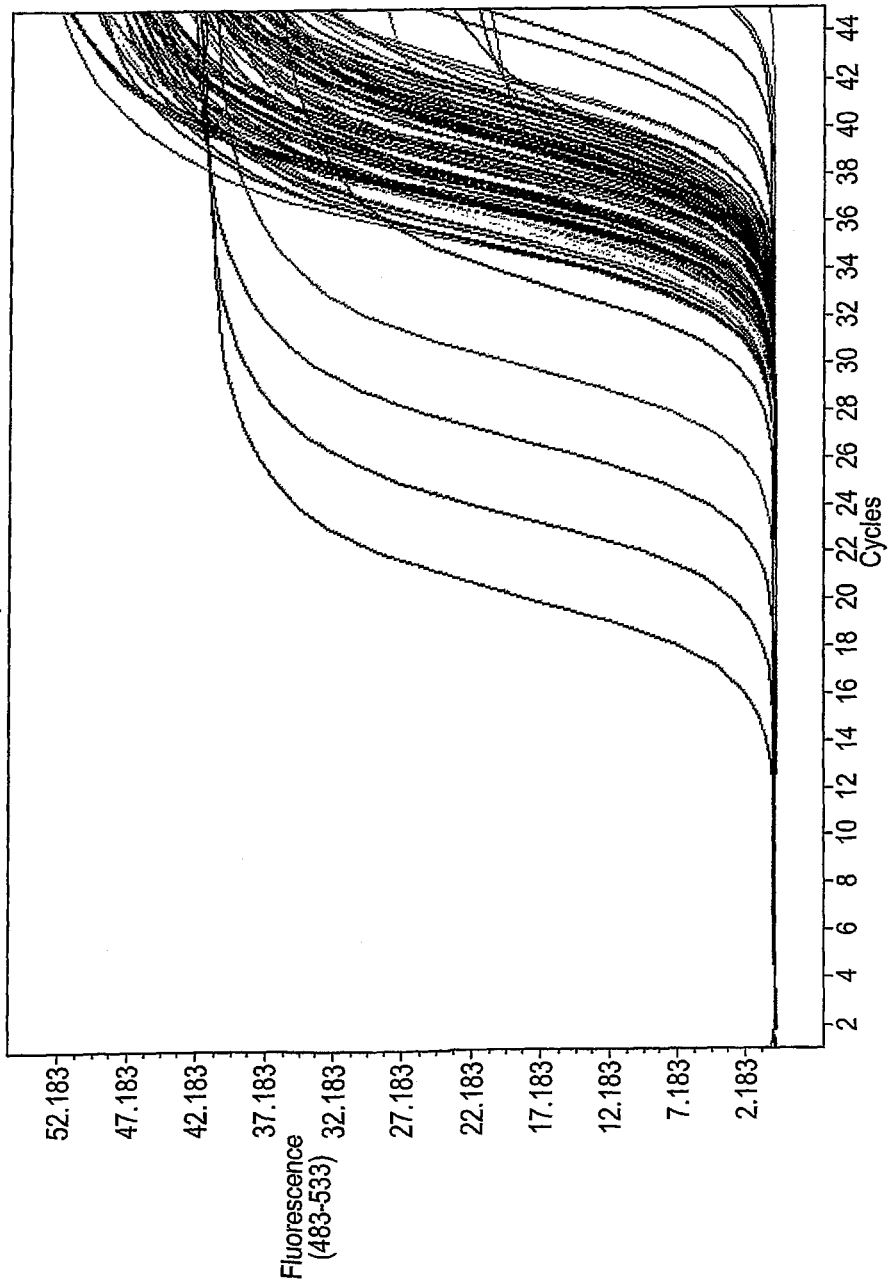

Melting Peaks

Amplification Curves

RAPID DETECTION OF MYCOBACTERIA

CROSS-REFERENCE TO RELATED APPLICATIONS

This application is the National Stage of International Application No. PCT/GB2009/050355 filed Apr. 9, 2009, which claims the benefit of Patent Application No. GB0806431.3, filed Apr. 9, 2008, in Great Britain, the disclosures of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Apr. 10, 2013, is named MATS-0003_SL.txt and is 15,560 bytes in size.

The present invention relates to a method for rapid detection of mycobacteria in a sample, and to reagents and kits therefor.

As the aetiological agent of tuberculosis infection (TB), *Mycobacterium tuberculosis* (*M. tuberculosis*) is the leading cause of death by infectious disease worldwide—latent infection affecting as much as one third of the world's population. The World Health Organisation (WHO) estimates that nearly nine million new cases of TB, and nearly two million deaths, occur globally each year. The largest number of new TB cases in 2005 occurred in South-East Asia (34% of incident cases globally), and the estimated incidence rate in sub-Saharan Africa is nearly 350 cases per 100,000 population.

However, TB infection is not limited to the developing world: the UK has seen a resurgence of tuberculosis since the late 1980s and there are currently over 8000 new cases each year—a rate of 14.0 per 100,000 population. About 40% of these new cases occur in the London region, where the rate of infection is 44.8 per 100,000 population. High risk populations include some migrant groups, the homeless, prisoners and problem drug users.

TB infection can normally be treated by a 6 month course of antibiotics; however patient compliance to drug treatment is varied, with patients often stopping therapy when their symptoms cease. In addition, TB rates are high amongst migrant populations, rendering follow-up treatments harder to administer. Left untreated, each person with active TB disease will infect on average between 10 and 15 people every year. A comprehensive strategy endorsed by the WHO, termed "Directly Observed Therapy Short-course" (DOTS) is an approach to increase drug compliance and reduce the emergence of multi drug-resistant *M. tuberculosis* strains. One aspect of this WHO approach focuses on enabling and promoting research, recognising that elimination of TB will depend on new diagnostics, drugs and vaccines.

Because optimal patient management requires early initiation of drug therapy and isolation of infectious individuals as soon as possible, there is a need in the art for rapid and reliable detection techniques.

However, traditional methods for the diagnosis of TB infection are either prolonged (organism culture), or potentially lacking in sensitivity (acid fast smear microscopy). The diagnosis of extra-pulmonary TB is complicated by the difficulty in obtaining adequate material for examination using known techniques.

In more detail, the current standard methodology for detecting mycobacteria requires skilled technicians and can result in up to eight weeks delay for a diagnostic result. Current WHO guidelines recommend that people with suspected TB submit at least three sputum samples (produced on separate occasions) to increase the likelihood of detecting active TB.

In order to detect mycobacteria in sputum by Ziehl Neelsen staining, over 5,000 organisms per ml sputum are needed to visualize the bacilli by light microscopy. As such, the 'smear' test often lacks both sensitivity and specificity. Moreover, in patients with active pulmonary TB, only an estimated 45% of infections are detected by sputum microscopy (Dye et al., 2005).

Culture of mycobacteria remains the gold standard for both diagnosis and drug sensitivity testing and may detect as few as 10 organisms per ml of sputum. However, this technique is hampered by both long incubation times (up to several weeks for diagnosis) and a difficulty to implement in the field (Kent & Kubica, 1985).

The *Mycobacterium tuberculosis* complex (MTBc) comprises five species: *M. tuberculosis, M. microti, M. bovis, M. canetti*, and *M. africanum*—which are the causative agent in the majority of cases of *Mycobacterium tuberculosis* infection (TB) throughout the world. The high level of DNA sequence identity between these species has limited the use of DNA sequences to differentiate between members of the MTBc.

Since the introduction of nucleic acid amplification assays in the field of diagnostic mycobacteriology, a number of in-house and commercial assays have been developed. By way of example, the Roche AMPLICOR® MTB system amplifies a 584-bp region of the 16S rRNA gene sequence common to all mycobacteria.

Current molecular methodologies for detecting and typing mycobacteria of the MTB complex "MTBc" include amplification of the transposable element IS6110 (Thierry et al., 1990; Yuen et al., 1995). However, IS6110-based methods suffer from poor reproducibility and poor sensitivity.

In this regard, the copy number of IS6110 varies between members of the MTBc, and appears to be strain dependent (Poulet & Cole, 1995). Whereas many members of the MTBc contain 8-15 copies of IS6110 scattered throughout the genome, about 40% of *M. tuberculosis* strains possess only one or two copies of the element, and *M. bovis* contains (on average) only a single copy.

In the late 1990s, the simultaneous detection and strain differentiation of mycobacteria was reported using a PCR-based technique termed "spacer oligotyping" (spoligotyping), based on detecting the presence or absence of 43 known polymorphic 'spacer' regions of 25-41 bp within the 36 bp direct repeat (DR) locus present exclusively in MTBc strains (Kamerbeek et al., 1997). Strains vary in the total amount of DRs in the genome and the presence or absence of particular spacer regions. Thus, like IS6110-based methods, spoligotyping lacks discriminatory power.

"Mycobacterial Interspersed Repetitive Units" (MIRUs) are variable number tandem repeat sequences (VNTRs) scattered over about 41 loci located throughout the genome of MTBc mycobacteria. Each MIRU locus contains a variable number of MIRU repeat sequence elements in tandem (up to about 13 repeat elements per locus).

Supply et al., 2001, has described a method for genotyping *M. tuberculosis* strains, based on determining the number of tandem repeats at MIRU loci in the *M. tuberculosis* genome. The method described in Supply et al. comprises PCR amplification using primers specific for regions of the *M. tuberculosis* genome that flank the MIRU loci. The sizes of the generated amplicons reflect the numbers of repeats at each MIRU locus.

There is a need in the art for a rapid, simple, specific and highly sensitive molecular method to detect mycobacteria in samples such as sputum and respiratory specimens, at levels as low as a single genome copy—preferably an 'on-the-spot' technique that would easily be transported into the field, for example in the developing world.

The present invention meets this need by providing a method for detecting a *mycobacterium* belonging to the MTB complex in a sample, the method comprising:
  (a) contacting the sample with a pair of forward and reverse oligonucleotide primers;
    wherein said forward primer hybridises to a target nucleic acid sequence located within a Mycobacterial Interspersed Repetitive Unit (MIRU) repeat element; and
    wherein said reverse primer hybridises to a target nucleic acid sequence located within a Mycobacterial Interspersed Repetitive Unit (MIRU) repeat element;
  (b) extending said forward and reverse primers to generate an amplification product; and
  (c) detecting the amplification product.

The method advantageously provides a highly sensitive, rapid and robust molecular diagnostic assay for mycobacteria of the *M. tuberculosis* complex (MTBc) such as *M. tuberculosis* or *M. bovis*.

The particular arrangement of MIRU repeats throughout the genome of MTBc mycobacteria substantially increases the sensitivity of the assay.

In one embodiment, results advantageously can be obtained from the assay in under two hours. In one embodiment, the assay advantageously enables single molecule detection directly from sputa. In one embodiment, results advantageously can be obtained directly from micro-volumes of a patient sample (eg. sputum) without the requirement of a time-consuming nucleic acid extraction procedure.

Hence, in one embodiment, the assay dramatically reduces waiting times and theoretically permits near-patient testing.

A further advantage of the presently claimed assay is its simplicity—it can preferably be performed and read by non-specialist personnel and is non-labour intensive.

MIRU repeat elements comprise nucleic acid sequence that is specific to members of the MTB complex.

Thus, in one embodiment, the detection method of the present invention is based on amplification of this MTBc-specific nucleic acid sequence.

In one embodiment, the target nucleic acid sequence to which the forward primer hybridises is specific to mycobacteria of the MTB complex. In one embodiment, the target nucleic acid sequence to which the reverse primer hybridises is specific to mycobacteria of the MTB complex In one embodiment, extension of the forward and reverse primers generates an amplification product comprising MTB complex-specific nucleic acid sequence.

In one embodiment, the amplification product comprising MTB complex-specific nucleic acid sequence is detected.

In one embodiment, the target nucleic acid sequence to which the forward primer hybridises is not located within a MIRU4 repeat element (also known as an ETRD repeat element). In one embodiment, the target nucleic acid sequence to which the reverse primer hybridises is not located within a MIRU4 repeat element (also known as an ETRD repeat element). In one embodiment, neither the forward primer nor the reverse primer hybridises to a target nucleic acid sequence located within a MIRU4 repeat element. In one embodiment, the amplification product does not comprise a MIRU4 repeat element nucleic acid sequence.

In one embodiment, the MIRU repeat element has at least 90% sequence identity (preferably 91, 92, 93, 94, 95, 96, 97, 98, 99 or 100% sequence identity) to a MIRU repeat element selected from MIRU2 repeat elements, MIRU10 repeat elements, MIRU16 repeat elements, MIRU23 repeat elements, MIRU24 repeat elements, MIRU26 repeat elements, MIRU27 repeat elements (also known as QUB5 repeat elements), MIRU31 repeat elements (also known as ETRE repeat elements) and MIRU39 repeat elements.

Thus, in one embodiment, the forward primer hybridises to a target nucleic acid sequence located within a MIRU repeat element, wherein said MIRU repeat element has at least 90% sequence identity (preferably 91, 92, 93, 94, 95, 96, 97, 98, 99 or 100% sequence identity) to a MIRU repeat element selected from MIRU2 repeat elements, MIRU10 repeat elements, MIRU16 repeat elements, MIRU23 repeat elements, MIRU24 repeat elements, MIRU26 repeat elements, MIRU27 repeat elements (also known as QUB5 repeat elements), MIRU31 repeat elements (also known as ETRE repeat elements) and MIRU39 repeat elements. In one embodiment, said target nucleic acid sequence is specific to mycobacteria of the MTB complex.

In one embodiment, the reverse primer hybridises to a target nucleic acid sequence located within a MIRU repeat element, wherein said MIRU repeat element has at least 90% sequence identity (preferably 91, 92, 93, 94, 95, 96, 97, 98, 99 or 100% sequence identity) to a MIRU repeat element selected from MIRU2 repeat elements, MIRU10 repeat elements, MIRU16 repeat elements, MIRU23 repeat elements, MIRU24 repeat elements, MIRU26 repeat elements, MIRU27 repeat elements (also known as QUB5 repeat elements), MIRU31 repeat elements (also known as ETRE repeat elements) and MIRU39 repeat elements. In one embodiment, said target nucleic acid sequence is specific to mycobacteria of the MTB complex.

By way of example, the genome of the CDC1551 strain of *M. tuberculosis* comprises 3 tandem repeat elements at the MIRU2 locus, 5 tandem repeat elements at the MIRU10 locus, 3 tandem repeat elements at the MIRU16 locus, 5 tandem repeat elements at the MIRU23 locus, 1 tandem repeat element at the MIRU24 locus, 5 tandem repeat elements at the MIRU26 locus, 4 tandem repeat elements at the MIRU27/QUB5 locus, 3 tandem repeat elements at the MIRU31/ETRE locus, and 2 tandem repeat elements at the MIRU39 locus.

Thus, in one embodiment, the forward primer hybridises to a target nucleic acid sequence located within a MIRU repeat element, wherein said MIRU repeat element has at least 90% sequence identity (preferably 91, 92, 93, 94, 95, 96, 97, 98, 99 or 100% sequence identity) to a MIRU repeat element selected from (with reference to the CDC1551 strain of *M. tuberculosis*):
  MIRU2 repeat elements 1, 2 and 3;
  MIRU10 repeat elements 1, 2, 3, 4 and 5;
  MIRU16 repeat elements 1, 2 and 3;
  MIRU23 repeat elements 1, 2, 3, 4 and 5;
  MIRU24 repeat element 1;
  MIRU26 repeat elements 1, 2, 3, 4 and 5;
  MIRU27/QUB5 repeat elements 1, 2, 3 and 4 (preferably MIRU27/QUB5 tandem repeat elements 2, 3 and 4);
  MIRU31/ETRE repeat elements 1, 2 and 3 (preferably MIRU31/ETRE repeat elements 2 and 3); and
  MIRU39 repeat elements 1 and 2.

In one embodiment, the reverse primer hybridises to a target nucleic acid sequence located within a MIRU repeat element, wherein said MIRU repeat element has at least 90% sequence identity (preferably 91, 92, 93, 94, 95, 96, 97, 98, 99 or 100% sequence identity) to a MIRU repeat element selected from (with reference to the CDC1551 strain of *M. tuberculosis*):
MIRU2 repeat elements 1, 2 and 3;
MIRU10 repeat elements 1, 2, 3, 4 and 5;
MIRU16 repeat elements 1, 2 and 3;
MIRU23 repeat elements 1, 2, 3, 4 and 5;
MIRU24 repeat element 1;
MIRU26 repeat elements 1, 2, 3, 4 and 5;
MIRU27/QUB5 repeat elements 1, 2, 3 and 4 (preferably MIRU27/QUB5 tandem repeat elements 2, 3 and 4);
MIRU31/ETRE repeat elements 1, 2 and 3 (preferably MIRU31/ETRE repeat elements 2 and 3); and
MIRU39 repeat elements 1 and 2.

In one embodiment, said MIRU repeat element comprises (and may consist of) a nucleotide sequence having at least 90% sequence identity (preferably 91, 92, 93, 94, 95, 96, 97, 98, 99 or 100% sequence identity) to a nucleotide sequence selected from SEQ ID NOs: 1-24 (as shown below in Table 1) or the complement thereof.

TABLE 1

| SEQ ID NO: | Sequence (5' to 3') |
|---|---|
| 1 | AGGCGCCGCTCCTCCTCATCGCTTCGCTGTGCATCGTCG CTGGCGCGAGTCA |
| 2 | TAGGCGCCGCTCCTCCTCATCGCTTCGCTGTGCATCGTC GCCGGCGCGAGTCA |
| 3 | TAGGCGCCGCTCTCCCCCGCAAGTGGGAGGTGCCCCCA CCTCATGTGTGGTCAACT |
| 4 | ATGGCGCCGCTCCTCCTCATCGCTGCGCTCTGCATCGTC GCCGGCGGTAGTTA |
| 5 | ATGGCGCCGCTCCTCCTCATCGCTGCGCTCTGCATCGTC GCCGGCGGTAGTCA |
| 6 | ATGGCGCCGCTCCTCCTCATCGCTGCGCTCTGCATCGTC GCCGGCGCGGGGGTCAT |
| 7 | GCCGCTCCTCCTCATCGCTTCGCTCTGCATCGTCGTCGG CGCGGTTCA |
| 8 | CGAGCGCCGCTCCTCCTCATCGCTTCGCTCTGCATCGTC GTCGGCGCGGTTCA |
| 9 | CGAGCGCCGCTCCTCCTCATCGCTTCGCTCTGCATCGTC GTCGGCGCGGCTCACGTGG |
| 10 | TGCGCCGCTCCTCCTCATCGCTTCGCTCTGCATCGTCAC CGGCGCGACTCA |
| 11 | TCTGCGCCGCTCCTCCTCATCGCTTCGCTCTGCATCGTC ACCGGCGCGACTCA |
| 12 | TCTGCGCCGCTCCTGCTCATCGCTTCGCTCTGCATCGTC ACCGGCGCGACTCA |
| 13 | TCTGCGCCGCTCCTCTCATCGCTTCGCTCTGCATCGTCA CCGGCGCGCATGGTCAGCG |
| 14 | CTTCGATATGGCGCCGCTCCTCAGCATCGCTGCGCTCTG CATCGTCGCCGGCGC |
| 15 | AAGCGCCGCTCCTCCTCATCGCTGCGCTCTGCATCGTCG CCGGCGGAGGTCA |
| 16 | AGCGCCGCTCCTCCTCATCGCTGCGCTCTGCATCGTCGC CGGCGGAGGTCA |
| 17 | GCGCCGCTCCTCCTCATCGCTGCGCTCTGCATCGTCGCC GGCGGAGGTCACAGA |

TABLE 1-continued

| SEQ ID NO: | Sequence (5' to 3') |
|---|---|
| 18 | CTGGCGCCGCTCCTCCCCATCGCTTTGCTCTGCATCGTC GCCGGCGCGGGTCACTGGC |
| 19 | CTGGCGCCGCTCCTCCCCATCGCTTTGCTCTGCATCGTC GCCGGCGCGGGTCA |
| 20 | CTGGCGCCGCTCCTCCCCATCGCTTTGCTCTGCATCGTC GCCGGCGCGGGTCAATCG |
| 21 | TCTGCGCCGCTCCTCCTCATCGCTGCGCTCTGCATCGTC GCCGGCGCCAACCA |
| 22 | TCTGCGCCGCTCCTCCTCATCGCTGCGCTCTGCATCGTC GCCGGCGCGAAGCAGCG |
| 23 | GCGCCGCTCCTCCTCATCGCTGCGCTTTGCATCGTCGCC GGCGCGGGCCG |
| 24 | TTGGCGCCGCTCCTCCTCATCGCTGCGCTTTGCATCGTC GCCGGCGCGGGTCA |

Variants of MIRU repeat element nucleotide sequences may alternatively be defined by reciting the number of nucleotides that differ between the variant sequence and a reference MIRU repeat element nucleotide sequence SEQ ID NO provided in Table 1, above. Thus, in one embodiment, the MIRU repeat element comprises (and may consist of) a nucleotide sequence that differs from SEQ ID NOs: 1-24 (or the complement thereof) at no more than 5 nucleotide positions, preferably at no more than 4, 3, 2 or 1 nucleotide positions.

In general, a reverse primer is designed to hybridise to a target nucleic acid sequence within the coding (sense) strand of a target nucleic acid, and a forward primer is designed to hybridise to a target nucleic acid sequence within the complementary (ie. anti-sense) strand of the target nucleic acid.

The term "complement of a nucleic acid sequence" refers to a nucleic acid sequence having a complementary nucleotide sequence and reverse orientation as compared to a reference nucleotide sequence.

The forward primer hybridises to a target nucleic acid sequence (a 'forward primer target sequence') located within the sequence of a MIRU repeat element.

In one embodiment, the forward primer target sequence has a length in the range of 10-40 consecutive nucleotides of the MIRU repeat element, preferably at least 11, 12, 13, 14, 15, 16, 17, 18, 19, 20, 21 or 22 consecutive nucleotides of the MIRU repeat element, preferably up to 38, 35, 32, 30, 29, 28, 27, 26, 25, 24, 23 or 22 consecutive nucleotides of the MIRU repeat element. More preferably, the forward primer target sequence has a length of 17-27 consecutive nucleotides of the MIRU repeat element, most preferably a length of about 22 consecutive nucleotides of the MIRU repeat element.

In one embodiment, the forward primer target sequence is specific to mycobacteria of the MTB complex.

The reverse primer hybridises to a target nucleic acid sequence (a 'reverse primer target sequence') located within the sequence of a MIRU repeat element.

In one embodiment, the reverse primer target sequence has a length in the range of 10-40 consecutive nucleotides of the MIRU repeat element, preferably at least 11, 12, 13, 14, 15, 16, 17, 18, 19 or 20 consecutive nucleotides of the MIRU repeat element, preferably up to 38, 35, 32, 30, 29, 28, 27, 26, 25, 24, 23, 22, 21 or 20 consecutive nucleotides of the MIRU repeat element. More preferably, the reverse primer target sequence has a length of 15-25 consecutive nucleotides of the MIRU repeat element, most preferably a length of about 20 consecutive nucleotides of the MIRU repeat element.

In one embodiment, the reverse primer target sequence is specific to mycobacteria of the MTB complex.

In one embodiment, the forward primer hybridises to a target nucleic acid sequence that comprises (or consists of) the complement of a nucleotide sequence selected from SEQ ID NOs: 25-39, as shown in Table 2 below, or a nucleotide sequence that is at least 90% identical thereto (preferably 91, 92, 93, 94, 95, 96, 97, 98 or 99% identical thereto), or a fragment thereof.

TABLE 2

| SEQ ID NO: | Forward primer target nucleotide sequence (5'→3') |
|---|---|
| 25 | GGCGCCGCTCCTCCTCATCGCT |
| 26 | GGCGCCGCTCTCCCCGCAAGT |
| 27 | GGCGCCGCTCCTCCTCATCGCT |
| 28 | GCCGCTCCTCCTCATCGCT |
| 29 | AGCGCCGCTCCTCCTCATCGCT |
| 30 | TGCGCCGCTCCTCCTCATCGCT |
| 31 | TGCGCCGCTCCTGCTCATCGCT |
| 32 | TGCGCCGCTCCTCTCATCGCT |
| 33 | GGCGCCGCTCCTCAGCATCGCT |
| 34 | AGCGCCGCTCCTCCTCATCGCT |
| 35 | GCGCCGCTCCTCCTCATCGCT |
| 36 | GGCGCCGCTCCTCCCCATCGCT |
| 37 | TGCGCCGCTCCTCCTCATCGCT |
| 38 | GGCGCCGCTCCTCCTCATCGCT |
| 39 | GCGCCGCTCCTCCTCATCGCT |

In one embodiment, a fragment of the complement of SEQ ID NOs: 25-27, 29-31, 33-34 or 36-38 (or sequence variants thereof as defined above), has at least 19, 20 or 21 consecutive nucleotides thereof. In one embodiment, a fragment of the complement of SEQ ID NO: 28 (or sequence variants thereof as defined above), has at least 16, 17 or 18 consecutive nucleotides thereof. In one embodiment, a fragment of the complement of SEQ ID NOs: 32, 35 or 39 (or sequence variants thereof as defined above), has at least 18, 19 or 20 consecutive nucleotides thereof.

In one embodiment, the reverse primer hybridises to a target nucleic acid sequence that comprises (or consists of) a nucleotide sequence that is at least 90% identical to (preferably 91, 92, 93, 94, 95, 96, 97, 98, 99 or 100% identical to) a nucleotide sequence selected from SEQ ID NOs: 40-46 (as shown in Table 3, below), or a fragment thereof.

TABLE 3

| SEQ ID NO: | Reverse primer target nucleotide sequence (5'→3') |
|---|---|
| 40 | GCTGTGCATCGTCGCTGGCG |
| 41 | GCTGTGCATCGTCGCCGGCG |
| 42 | GAGGTGCCCCCACCTCATGT |

TABLE 3-continued

| SEQ ID NO: | Reverse primer target nucleotide sequence (5'→3') |
|---|---|
| 43 | GCTCTGCATCGTCGCCGGCG |
| 44 | GCTCTGCATCGTCGTCGGCG |
| 45 | GCTCTGCATCGTCACCGGCG |
| 46 | GCTTTGCATCGTCGCCGGCG |

In one embodiment, a fragment of SEQ ID NOs: 40-46 (or sequence variants thereof as defined above), has at least 17, 18 or 19 consecutive nucleotides thereof.

In one embodiment, the forward primer is 15-30 nucleotides long, preferably at least 16, 17, 18, 19, 20, 21 or 22 nucleotides long, preferably up to 29, 28, 27, 26, 25, 24, 23 or 22 nucleotides long. More preferably, the forward primer is about 20-24 nucleotides long and most preferably about 22 nucleotides long.

In one embodiment, the reverse primer is 15-30 nucleotides long, preferably at least 16, 17, 18, 19 or 20 nucleotides long, preferably up to 29, 28, 27, 26, 25, 24, 23, 22, 21 or 20 nucleotides long. More preferably, the reverse primer is 18-22 nucleotides long and most preferably about 20 nucleotides long.

In one embodiment, the forward primer comprises (or consists of) a nucleotide sequence having at least 80% identity to (preferably at least 82, 85, 86, 87, 88, 89, 90 91, 92, 93, 94, 95, 96, 97, 98, 99 or 100% identity to) a nucleotide sequence selected from SEQ ID NOs: 25-39 (as shown in Table 2 above). Conservative substitutions are preferred.

In one embodiment, the forward primer comprises (or consists of) a nucleotide sequence having at least 80% identity to (preferably at least 82, 85, 86, 87, 88, 89, 90 91, 92, 93, 94, 95, 96, 97, 98, 99 or 100% identity to) a nucleotide sequence selected from SEQ ID NOs: 47 or 48 (as shown in Table 4A below). Conservative substitutions are preferred.

TABLE 4A

| FORWARD PRIMER SEQ ID NO: | SEQUENCE |
|---|---|
| 47 | GGC GCC GCT CCT CCT CAT CGC T |
| 48 | GGC GCC GCT CCT CCC CAT CGC T |

Variants of the specific forward primer sequences provided above may alternatively be defined by reciting the number of nucleotides that differ between the variant sequences and the specific forward primer reference sequence SEQ ID NOs provided above. Thus, in one embodiment, the forward primer may comprise (or consist of) a nucleotide sequence that differs from SEQ ID NOs: 25-39 or 47-48 at no more than 4 nucleotide positions, preferably at no more than 3, 2 or 1 nucleotide positions. Conservative substitutions are preferred.

Fragments of the above-mentioned forward primer sequences (and sequence variants thereof as defined above) may also be employed.

In one embodiment, the forward primer may comprise (or consist of) a fragment of SEQ ID NOs: 25-39, 47 or 48 (and sequence variants thereof as defined above), wherein said fragment preferably comprises at least 15 consecutive nucleotides thereof, more preferably at least 16, 17, 18, 19, 20 or 21 consecutive nucleotides thereof.

In one embodiment, the reverse primer comprises (or consists of) a nucleotide sequence having at least 80% identity to (preferably 82, 85, 86, 87, 88, 89, 90, 91, 92, 93, 94, 95, 96, 97, 98, 99 or 100% identity to) the complement of a nucleotide sequence selected from SEQ ID NOs: 40-46, as shown in Table 3 above. Conservative substitutions are preferred.

In one embodiment, the reverse primer comprises (or consists of) a nucleotide sequence having at least 80% identity to (preferably 85, 86, 87, 88, 89, 90, 91, 92, 93, 94, 95, 96, 97, 98, 99 or 100% identity to) a nucleotide sequence selected from SEQ ID NOs: 49, 50 or 51, as shown in Table 4B below. Conservative substitutions are preferred.

TABLE 4B

| REVERSE PRIMER SEQ ID NO: | SEQUENCE |
| --- | --- |
| 49 | CGC CGG CGA CGA TGC AGA GC |
| 50 | CGC CGG TGA CGA TGC AGA GC |
| 51 | CGC CGG CGA CGA TGC AAA GC |

Variants of the specific reverse primer sequences provided above may alternatively be defined by reciting the number of nucleotides that differ between the variant sequences and the specific reverse primer reference sequence SEQ ID NOs provided above. In one embodiment, the reverse primer may comprise (or consist of) a nucleotide sequence that differs from SEQ ID NOs: 49, 50 or 51 (or from the complement of SEQ ID NOs: 40-46) at no more than 4 nucleotide positions, preferably at no more than 3, 2 or 1 nucleotide positions. In this regard, conservative substitutions are preferred.

Fragments of the above-mentioned reverse primer sequences (and sequence variants thereof as defined above) may also be employed.

In one embodiment, the reverse primer may comprise (or consist of) a fragment of SEQ ID NOs: 49-51, or a fragment of the complement of SEQ ID NOs: 40-46, (and sequence variants thereof as defined above), wherein said fragment preferably comprises at least 15 consecutive nucleotides thereof, more preferably at least 16, 17, 18 or 19 consecutive nucleotides thereof.

The forward and reverse primers of the present invention are designed to bind to the target nucleic acid sequence based on the selection of desired parameters, using conventional software, such as Primer Express (Applied Biosystems).

The forward primer is preferably sequence-specific and preferably hybridises specifically to the target nucleic acid sequence within the MIRU repeat element. The reverse primer is preferably sequence-specific and preferably hybridises specifically to the target nucleic acid sequence within the MIRU repeat element.

The term 'hybridises' is equivalent and interchangeable with the term 'binds'.

It is preferred that the binding conditions are such that a high level of specificity is provided. The melting temperature (Tm) of the forward and reverse primers is preferably in excess of 68° C. and is most preferably about 72° C.

In one embodiment, there are regions of nucleotide sequence complementarity between the sequences of the forward and reverse primers. These complementary sequence regions enable primers to hybridise to each other by complementary base pairing, to form "primer dimers". In one embodiment, these primer-primer dimers provide an internal control in the detection assay.

In one embodiment, there are from 1 to 10 complementary bases between the forward and reverse primers. Thus, in one embodiment, the forward and reverse primers are able to hybridise to each other via complementary base pairing at from 1 to 10 positions, preferably at from 1 to 10 consecutive nucleotide positions. In one embodiment, the forward and reverse primers have at least 2, 3, 4, 5, 6, 7, 8, 9 or 10 complementary bases (preferably at least 2, 3, 4, 5, 6, 7, 8, 9 or 10 consecutive complementary bases). The complementary bases may be located anywhere within the forward and reverse primers, for example, towards the 3' ends of the forward and reverse primers. In one embodiment, the 1-10 nucleotides closest to the 3' terminus of the forward and reverse primers are complementary. Preferably, the 2, 3, 4, 5 or 6 nucleotides closest to the 3' terminus of the forward and reverse primers are complementary, most preferably the 3 nucleotides closest to the 3' terminus of the forward and reverse primers are complementary.

In one embodiment, primer-primer hybridisation of forward and reverse primers forms dimers that are 15-45 bp long, preferably at least 20, 25, 30, 31, 32, 33, 34, 35 or 36 bp long, preferably up to 44, 43, 42, 41, 40, 39, 38, 37 or 36 bp long. Preferably the forward primer-reverse primer dimers are 30-40 bp long, more preferably about 34-38 bp long, most preferably about 36 bp long.

In one embodiment, the forward primer and/or the reverse primer comprises a tag or label. In one embodiment, said tag or label is incorporated into the amplification product when the primer is extended. The tag or label is preferably located at the 5' or 3' end of the forward and/or reverse primer, most preferably at the 5' end of the reverse primer.

Examples of suitable labels include detectable labels such as radiolabels or fluorescent or coloured molecules. By way of example, the label may be digoxygenin, fluorescein-isothiocyanate (FITC) or R-phycoerythrin. The label may be a reporter molecule, which is detected directly, such as by exposure to photographic or X-ray film. Alternatively, the label is not directly detectable, but may be detected indirectly, for example, in a two-phase system. An example of indirect label detection is binding of an antibody to the label.

Examples of suitable tags include biotin and streptavidin. Other exemplary tags include receptors, ligands, antibodies, antigens, haptens and epitopes.

The sample is preferably a clinical sample (or is derived from a clinical sample) such as sputum, bronchoalveolar lavage, tracheal aspirate, lung tissue samples, cerebrospinal fluid, archaeological samples.

Amplification may be carried out using methods and platforms known in the art, for example PCR, such as real-time PCR, block-based PCR, ligase chain reaction, glass capillaries, isothermal amplification methods including loop-mediated isothermal amplification, rolling circle amplification transcription mediated amplification, nucleic acid sequence-based amplification, signal mediated amplification of RNA technology, strand displacement amplification, isothermal multiple displacement amplification, helicase-dependent amplification, single primer isothermal amplification, and circular helicase-dependent amplification.

In one embodiment, amplification can be carried using any amplification platform—as such, an advantage of this embodiment of the assay is that it is platform independent and not tied to any particular instrument.

In the presence of a suitable polymerase and DNA precursors (dATP, dCTP, dGTP and dTTP), the forward and reverse primers are extended in a 5' to 3' direction, thereby initiating the synthesis of new nucleic acid strands that are complementary to the individual strands of the target MTBc-specific nucleic acid. The primers thereby drive amplification of MTBc-specific nucleic acid sequence, thereby generating an amplification product comprising said MTBc-specific nucleic acid sequence. A skilled person would be able to determine suitable conditions for promoting amplification.

In this application, the expressions “amplification product”, “amplified nucleic acid sequence” and “amplicon” are used interchangeably and have the same meaning.

An individual MIRU repeat element comprises a target sequence for a forward primer as defined herein and a target sequence for a reverse primer as defined herein.

Thus, in one aspect, the forward and reverse primers hybridise to target nucleic acid sequences that are located within the same MIRU repeat element. In accordance with this aspect, extension of the forward and reverse primers generates an amplification product comprising nucleic acid sequence that is derived entirely from (ie. located entirely within) said individual MIRU repeat element.

Purely by way of example, in one embodiment, both the forward and reverse primers could bind their target nucleic acid sequences within MIRU10 repeat element 1. Extension from these primers would generate an amplification product comprising nucleic acid sequence derived entirely from MIRU10 repeat 1.

In one embodiment, the amplification product is about 30-55 nucleotides long, preferably at least about 32, 34, 35, 36, 37, 38, 39, 40, 41, 42, 43 or 44 nucleotides long, preferably up to about 54, 53, 52, 51, 50, 49, 48, 47, 46, 45 or 44 nucleotides long. More preferably, the amplification product is 40-50 nucleotides long, most preferably about 44 nucleotides long.

In most of the initial cycles of amplification, the forward and reverse primers will hybridise to the same MIRU repeat element, and will therefore amplify nucleic acid sequence that is located within a single MIRU repeat element, as discussed above.

However, in a multi-repeat MIRU locus, multiple repeat sequences comprise both a target nucleic acid sequence for a forward primer and a target nucleic acid sequence for a reverse primer. Hence, each multi-repeat MIRU locus comprises multiple target nucleic acid sequences for the forward and reverse primers.

Hence, the genome of MTB complex mycobacteria comprises multiple target nucleic acid sequences for the forward primer, and multiple target nucleic acid sequences for the reverse primer.

Successful amplification occurs by extension of a hybridised forward primer ‘downstream’ in a 5' to 3' direction towards a hybridised reverse primer and extension of said hybridised reverse primer ‘upstream’ in a 5' to 3' direction towards said forward primer—ie. the primers extend towards each other. In this regard, a reverse primer target sequence is said to be ‘downstream’ of a forward primer target sequence if the 3' end of a hybridised forward primer points towards the reverse primer target sequence, and 5' to 3' extension of said hybridised forward primer is in a direction towards the reverse primer target sequence. Likewise, a forward primer target sequence is said to be ‘upstream’ of a reverse primer target sequence if the 3' end of a hybridised reverse primer points towards the forward primer target sequence, and 5' to 3' extension of said hybridised reverse primer is in a direction towards the forward primer target sequence.

In one aspect, forward and reverse primers hybridise to target sequences that are located within different MIRU repeat elements, at the same MIRU locus.

As illustrated in FIG. 1, a MIRU locus comprising 5 repeat elements in tandem comprises 5 potential target nucleic acid sequences for hybridisation of the forward primer and 5 potential target nucleic acid sequences for hybridisation of the reverse primer. In this regard, repeats 4 and 5 of the MIRU locus are “downstream” of repeat 3 and repeats 1 and 2 of the MIRU locus are “upstream” of repeat 3.

Thus, a forward primer hybridised to repeat 1 of a 5-repeat locus may pair for amplification with a reverse primer hybridised to repeat 1, 2, 3, 4 or 5, whereas a forward primer hybridised to repeat 3 of a 5-repeat locus may only pair for amplification with a reverse primer hybridised to repeat 3, 4 or 5.

However, a forward primer cannot pair successfully for amplification with a reverse primer that is hybridised further upstream. In this regard, a forward primer hybridised to repeat 3 of a 5-repeat locus and a reverse primer hybridised to repeat 1 or 2 will be extended away from each other in opposite directions, which will not result in successful amplification.

By way of example (as illustrated in FIG. 1), amplification may occur by extension from a forward primer that hybridises to its target nucleic acid sequence in the $1^{st}$ repeat of a 5-repeat MIRU locus and extension from a reverse primer that hybridises to its target nucleic acid sequence in the $1^{st}$, $2^{nd}$, $3^{rd}$, $4^{th}$ or $5^{th}$ or repeat of the 5-repeat locus.

Specifically, successful amplification may occur using the following combinations of forward and reverse primer target nucleic acid sequences (within the same MIRU locus):

| MIRU locus | Forward primer hybridises to: | Reverse Primer hybridises to: |
|---|---|---|
| MIRU2 | Repeat 1 | Repeat 1, 2 or 3 |
| | Repeat 2 | Repeat 2 or 3 |
| | Repeat 3 | Repeat 3 |
| | Repeat 1 | Repeat 1 |
| | Repeat 1 or 2 | Repeat 2 |
| | Repeat 1, 2 or 3 | Repeat 3 |
| MIRU10 | Repeat 1 | Repeat 1, 2, 3, 4 or 5 |
| | Repeat 2 | Repeat 2, 3, 4 or 5 |
| | Repeat 3 | Repeat 3, 4 or 5 |
| | Repeat 4 | Repeat 4 or 5 |
| | Repeat 5 | Repeat 5 |
| | Repeat 1 | Repeat 1 |
| | Repeat 1 or 2 | Repeat 2 |
| | Repeat 1, 2 or 3 | Repeat 3 |
| | Repeat 1, 2, 3 or 4 | Repeat 4 |
| | Repeat 1, 2, 3, 4 or 5 | Repeat 5 |
| MIRU16 | Repeat 1 | Repeat 1, 2 or 3 |
| | Repeat 2 | Repeat 2 or 3 |
| | Repeat 3 | Repeat 3 |
| | Repeat 1 | Repeat 1 |
| | Repeat 1 or 2 | Repeat 2 |
| | Repeat 1, 2 or 3 | Repeat 3 |
| MIRU23 | Repeat 1 | Repeat 1, 2, 3, 4 or 5 |
| | Repeat 2 | Repeat 2, 3, 4 or 5 |
| | Repeat 3 | Repeat 3, 4 or 5 |
| | Repeat 4 | Repeat 4 or 5 |
| | Repeat 5 | Repeat 5 |
| | Repeat 1 | Repeat 1 |
| | Repeat 1 or 2 | Repeat 2 |
| | Repeat 1, 2 or 3 | Repeat 3 |
| | Repeat 1, 2, 3 or 4 | Repeat 4 |
| | Repeat 1, 2, 3, 4 or 5 | Repeat 5 |
| MIRU24 | Repeat 1 | Repeat 1 |
| MIRU26 | Repeat 1 | Repeat 1, 2, 3, 4 or 5 |
| | Repeat 2 | Repeat 2, 3, 4 or 5 |
| | Repeat 3 | Repeat 3, 4 or 5 |
| | Repeat 4 | Repeat 4 or 5 |

-continued

| MIRU locus | Forward primer hybridises to: | Reverse Primer hybridises to: |
|---|---|---|
| | Repeat 5 | Repeat 5 |
| | Repeat 1 | Repeat 1 |
| | Repeat 1 or 2 | Repeat 2 |
| | Repeat 1, 2 or 3 | Repeat 3 |
| | Repeat 1, 2, 3 or 4 | Repeat 4 |
| | Repeat 1, 2, 3, 4 or 5 | Repeat 5 |
| MIRU27/QUB5 | Repeat 2 | Repeat 2, 3 or 4 |
| | Repeat 3 | Repeat 3 or 4 |
| | Repeat 4 | Repeat 4 |
| | Repeat 2 | Repeat 2 |
| | Repeat 2 or 3 | Repeat 3 |
| | Repeat 2, 3 or 4 | Repeat 4 |
| MIRU31/ETRE | Repeat 2 | Repeat 2 or 3 |
| | Repeat 3 | Repeat 3 |
| | Repeat 2 | Repeat 2 |
| | Repeat 2 or 3 | Repeat 3 |
| MIRU39 | Repeat 1 | Repeat 1 or 2 |
| | Repeat 2 | Repeat 2 |
| | Repeat 1 | Repeat 1 |
| | Repeat 1 or 2 | Repeat 2 |

In accordance with this aspect of the invention, extension from the forward and reverse primers amplifies a nucleic acid sequence that spans more than one adjacent MIRU repeat element in the same locus. Hence, in accordance with this aspect of the invention, the amplification product comprises nucleic acid sequence that spans more than one adjacent MIRU repeat element in the same locus.

In one embodiment, extension of the hybridised forward and reverse primers amplifies a nucleic acid sequence that spans 2 adjacent MIRU repeat elements in the locus. Hence, in accordance with this embodiment, the amplification product comprises nucleic acid sequence that spans 2 adjacent MIRU repeat elements in the same locus.

In one embodiment, extension of the hybridised forward and reverse primers amplifies a nucleic acid sequence that spans up to all the MIRU repeat elements in the locus (for example, spanning at least 2, 3, 4 or 5 MIRU repeat elements in the locus). Hence, in accordance with this embodiment, the amplification product comprises nucleic acid sequence that spans up to all the MIRU repeat elements in the locus (for example, spanning at least 2, 3, 4 or 5 MIRU repeat elements in the locus).

By way of example, in one embodiment, the forward primer binds its target sequence within MIRU10 repeat 1, and the reverse primer binds its target sequence within MIRU10 repeat 2, 3, 4 or 5. Extension from these primers would amplify a nucleic acid sequence that spans MIRU10 repeats 1 and 2 (if the reverse primer binds within MIRU10 repeat 2), or a nucleic acid sequence that spans MIRU10 repeats 1, 2 and 3 (if the reverse primer binds within MIRU10 repeat 3), or a nucleic acid sequence that spans MIRU10 repeats 1, 2, 3 and 4 (if the reverse primer binds within MIRU10 repeat 4), or a nucleic acid sequence that spans MIRU10 repeats 1, 2, 3, 4 and 5 (if the reverse primer binds within MIRU10 repeat 5).

In one embodiment, an amplification product that spans two MIRU repeats is 70-120 nucleotides long, preferably at least about 75, 80, 85, 90, 91, 92, 93, 94, 95, 96 or 97 nucleotides long, preferably up to about 110, 105, 104, 103, 102, 101, 100, 99, 98 or 97 nucleotides long. Most preferably an amplification product that spans two MIRU repeats is in the region of 90-105 nucleotides long, most preferably about 97 nucleotides long.

In one embodiment, an amplification product that spans three MIRU repeats is 100-200 nucleotides long, preferably at least about 105, 110, 115, 120, 125, 130, 135, 140, 145, 146, 147, 148, 149 or 150 nucleotides long, preferably up to about 195, 190, 185, 180, 175, 170, 165, 160, 155, 154, 153, 152, 151 or 150 nucleotides long. Most preferably an amplification product that spans two MIRU repeats is in the region of 135-165 nucleotides long, most preferably about 150 nucleotides long.

In one embodiment, an amplification product that spans four MIRU repeats is 145-240 nucleotides long, preferably at least about 150, 155, 160, 165, 170, 175, 180, 185, 190, 195, 196, 197, 198, 199, 200, 201, 202 or 203 nucleotides long, preferably up to about 235, 230, 225, 220, 215, 210, 209, 208, 207, 206, 205, 204 or 203 nucleotides long. Most preferably an amplification product that spans two MIRU repeats is in the region of 185-225 nucleotides long, most preferably about 203 nucleotides long.

In one embodiment, an amplification product that spans five MIRU repeats is 185-310 nucleotides long, preferably at least about 190, 195, 200, 205, 210, 215, 220, 225, 230, 235, 240, 245, 250, 251, 252, 253, 254, 255 or 256 nucleotides long, preferably up to about 305, 300, 295, 290, 285, 280, 275, 270, 265, 260, 259, 258, 257 or 256 nucleotides long. Most preferably an amplification product that spans two MIRU repeats is in the region of 235-285 nucleotides long, most preferably about 256 nucleotides long.

In one aspect, forward and reverse primers hybridise to target sequences that are located within different MIRU repeat elements.

In one embodiment, the different MIRU repeat elements are located within different MIRU loci scattered throughout the MTBc mycobacterial genome. In accordance with this aspect of the invention, 5' to 3' extension from the forward and reverse primers amplifies a nucleic acid sequence that spans MIRU repeat elements of adjacent MIRU locus. Hence, in accordance with this aspect of the invention, the amplification product comprises nucleic acid sequence that spans MIRU repeat elements of adjacent MIRU loci.

In one embodiment, the amplification products are very large molecules, which may be over 2 kb long, and may be over 5 kb long or even over 10 kb long (typically in the region of 11-12 kb long). In one embodiment, the amplification products are concatameric molecules.

The formation of these concatameric amplification products may be promoted by selection of suitable amplification conditions.

By way of example, the formation of concatameric molecules may be promoted by selecting an amplification protocol that limits hybridisation of the primers to the nucleic acid, thereby reducing the likelihood that all the potential primer target sequences will become occupied by a primer. By reducing the probability that primers will hybridise to all their potential target nucleic acid sequences, the probability of amplifying nucleic acid sequences located within a single MIRU repeat sequence is also reduced.

Thus, in one aspect, the formation of concatameric molecules is promoted by using a sub-saturating concentration of primers.

In one aspect, the formation of concatameric molecules is promoted by increasing the Tm. In one embodiment, the annealing Tm is substantially the same as the extension Tm (for example, about 72° C.). The use of a high annealing Tm is advantageous because MTBc nucleic acid is very GC-rich. At high Tm (eg. about 72° C.), very little non-specific extension occurs. In one embodiment, the time allowed for primer extension is reduced (for example, to about 2 seconds, 1.5 seconds or even 1 second). Reducing the primer extension time may also reduce the occurrence of primer-primer dimer artifacts.

In one aspect, the formation of concatameric molecules is promoted by selecting amplification conditions that promote incomplete extension of the forward and/or reverse primers.

In this regard, we have observed that primer extension products (particularly denatured incomplete/partial primer extension products) may behave as long primers in a subsequent round of amplification. By way of example, an incomplete extension product comprising a nucleic acid sequence spanning 3 MIRU repeats may anneal to a MIRU locus containing 2 MIRU repeats and act as an elongated primer. The amplification product generated by extension of the incomplete extension product/long primer will be a concatenated product spanning 4 MIRU repeats or 5 MIRU repeats (depending on whether the long primer binds to the first or second MIRU repeat in the 2-repeat MIRU locus).

In one aspect (illustrated in FIG. 2), extension products from the forward primers (including denatured partial extension products) hybridise to forward primer target sequences within a MIRU repeat at any MIRU locus, and act as elongated forward primers.

Likewise, in one aspect, extension products from the reverse primers (including denatured partial extension products) hybridise to reverse primer target sequences within a MIRU repeat at any MIRU locus, and act as elongated reverse primers.

The concatameric amplification products produced by extension of these elongated primers may thus comprise nucleic acid sequences located within multiple MIRU repeat elements from the same MIRU locus and/or from different MIRU loci.

The detection step may be carried out by any known means.

In one aspect, the amplification product is tagged or labelled, and the detection method comprises detecting the tag or label. The tag or label is preferably incorporated into the amplification product during the amplification step. In one embodiment, the forward and/or reverse primer comprises a tag or label, and the tag or label is incorporated into the amplification product when the primer is extended during the amplification step. The tag or label is preferably located at the 5' or 3' end of the forward or reverse primer, most preferably at the 5' end of the reverse primer.

Thus, in one embodiment, the amplification product is labelled, and the assay comprises detecting the label (preferably following removal of primer) and correlating presence of label with presence of amplification product, and hence the presence of mycobacteria of the MTBc. The label may comprise a detectable label such as a radiolabel or a fluorescent or coloured molecule. By way of example, the label may be digoxygenin, fluorescein-isothiocyanate (FITC) or R-phycoerythrin. The label may be a reporter molecule, which is detected directly, such as by exposure to photographic or X-ray film. Alternatively, the label is not directly detectable, but may be detected indirectly, for example, in a two-phase system. An example of indirect label detection is binding of an antibody to the label.

In one embodiment, the amplification product is tagged, and the assay comprises capturing the tag (preferably following removal of primer) and correlating presence of the tag with presence of amplification product, and hence the presence of mycobacteria of the MTBc. In one embodiment, the tag is captured using a capture molecule, which may be attached (eg. coated) onto a substrate or solid support, such as a membrane or magnetic bead.

Capture methods employing magnetic beads are advantageous because the beads (plus captured, tagged amplification product) can easily be concentrated and separated from the sample, using conventional techniques known in the art.

Examples of suitable tags include "complement/anti-complement pairs". The term "complement/anti-complement pair" denotes non-identical moieties that form a non-covalently associated, stable pair under appropriate conditions. For instance, biotin and avidin (or streptavidin) are members of a complement/anti-complement pair. Other exemplary complement/anti-complement pairs include receptor/ligand pairs, antibody/antigen (or hapten or epitope) pairs, and the like. Where subsequent dissociation of the complement/anti-complement pair is desirable, the complement/anti-complement pair preferably has a binding affinity of less than $10^9$ $M^{-1}$.

In one embodiment, the tag is selected from biotin and streptavidin. In this regard, a biotin tag may be captured using streptavidin, which may be coated onto a substrate or support such as a bead (for example a magnetic bead) or membrane. Likewise, a streptavidin tag may be captured using biotin, which may be coated onto a substrate or support such as a bead (for example a magnetic bead) or membrane. Other exemplary pairs of tags and capture molecules include receptor/ligand pairs and antibody/antigen (or hapten or epitope) pairs.

Thus, in one embodiment, the amplification product incorporates a biotin tag, and the detection step comprises contacting the sample with a streptavidin-coated magnetic bead, which captures the biotin-tagged amplification product.

The magnetic bead (plus captured, tagged amplification product) can then be separated from the sample, thereby separating the amplification product from the sample. The amplification product can then be detected by any known means.

In one embodiment, the nucleic acid sequence of the amplification product is determined. Sequencing of the amplification product may be carried out by any known means. For example (after melting off the unlabeled strand of DNA with sodium hydroxide), a colorimetric sequencing system may be employed, such as the Trimgen Mutector™ detection system.

In one aspect, the amplification product is detected by a method comprising contacting the sample with an oligonucleotide probe under conditions allowing the formation of hybridisation complexes between the probe and the amplification product, and detecting the hybridisation complexes. In one embodiment, the probe is specific for the amplification product.

The probe is preferably 5-30 nucleotides long, preferably at least 6, 7, 8, 9 or 10 nucleotides long. Preferably, the probe is up to 25 nucleotides long, more preferably up to 20, 18, 16, 15, 14, 13, 12, 11 or 10 nucleotides long. The probe is more preferably 8-12 nucleotides long, and most preferably about 10 nucleotides long. In this regard, the use of short probes enables faster annealing to the target nucleic acid.

The target nucleotide sequence to which the probe hybridises within the amplification product is preferably at least 5, 6, 7, 8, 9 or 10 nucleotides long. Preferably, the target sequence for the probe is up to 30 nucleotides long, more preferably up to 25, 20, 18, 16, 15, 14, 13, 12, or 11 nucleotides long. The probe target sequence is more preferably 8-12 nucleotides long, and most preferably about 10 nucleotides long.

In one embodiment, the probe is a PNA probe.

Probes are designed to hybridise to their target sequence within the amplification product based on a selection of desired parameters, using conventional software. It is preferred that the binding conditions are such that a high level of specificity is provided—ie. hybridisation of the probe to the amplification product occurs under "stringent conditions". In general, stringent conditions are selected to be about 5° C.

lower than the thermal melting point ($T_m$) for the specific sequence at a defined ionic strength and pH. The $T_m$ is the temperature (under defined ionic strength and pH) at which 50% of the target sequence hybridises to a perfectly matched probe. In this regard, the $T_m$ of probes of the present invention, at a salt concentration of about 0.02M or less at pH 7, is preferably above 60° C., more preferably about 70° C.

Premixed binding solutions are available (eg. EXPRESSHYB Hybridisation Solution from CLONTECH Laboratories, Inc.), and hybridisation can be performed according to the manufacturer's instructions. Alternatively, a person skilled in the art can devise suitable variations of these binding conditions.

It is preferable to screen the probes to minimise self-complementarity and dimer formation (probe-probe binding). Preferred probes of the present invention are selected so as to have minimal homology with human DNA. The selection process may involve comparing a candidate probe sequence with human DNA and rejecting the probe if the homology is greater than 50%. The aim of this selection process is to reduce annealing of probe to contaminating human DNA sequences and hence allow improved specificity of the assay.

In one embodiment, the sequence of the probe is 100% complementary to the sequence of the amplification product with which the probe hybridises. Alternatively, in one embodiment, up to about 30% (preferably up to about 25, 22, 20, 18, 16, 14, 12, 10, 9, 8, 7, 6, 5, 4, 3, 2 or 1%) of the probe nucleic acids may be mismatched as compared to the nucleic acid sequence of the amplification product, and nevertheless allow detection of the presence of the amplification product.

In one aspect, the oligonucleotide probe comprises (and by consist of) a nucleotide sequence having at least 80% identity (preferably at least 85, 90, 95 or 100% identity) to a nucleotide sequence selected from SEQ ID NOs: 52-57, as shown in Table 3, below. In this regard, conservative substitutions are preferred.

TABLE 3

| PROBE SEQ ID NO: | SEQUENCE |
| --- | --- |
| 52 | CTG CGC TCT G |
| 53 | CTT CGC TCT G |
| 54 | CTT CGC TGT G |
| 55 | CTG CGC TTT G |
| 56 | GTG GGA GGT G |
| 57 | CTT TGC TCT G |

An alternative means for defining variant probe sequences is by defining the number of nucleotides that differ between the variant sequence and the reference probe sequence. Thus, in one embodiment, a probe of the present invention comprises (or consists of) a nucleic acid sequence that differs from SEQ ID NOs: 52-57 by no more than 2 nucleotides, preferably by no more than 1 nucleotide. In this regard, conservative substitutions are preferred.

A fragment of the above-mentioned probe sequence may also be employed, wherein the fragment comprises at least 8 or 9 consecutive nucleotides of SEQ ID NOs: 52-57. Thus, in one embodiment, a probe of the present invention comprises (or consists of) a fragment of SEQ ID NOs: 52-57 (or sequence variants thereof as defined above), wherein said fragment preferably comprises at least 8 or 9 consecutive nucleotides thereof.

Following binding, washing under stringent (preferably highly stringent) conditions removes unbound oligonucleotides. Typical stringent washing conditions include washing in a solution of 0.5-2×SSC with 0.1% SDS at 55-65° C. Typical highly stringent washing conditions include washing in a solution of 0.1-0.2×SSC with 0.1% SDS at 55-65° C. A skilled person can readily devise equivalent conditions—for example, by substituting SSPE for the SSC in the wash solution.

In one embodiment, the probe comprises a label. Thus, in one embodiment, following hybridisation of labelled probe to amplification product, the label is associated with the bound amplification product. Thus, in one embodiment, the assay comprises detecting the label (preferably following removal of unbound probe) and correlating presence of label with presence of bound amplification product, and hence the presence of mycobacteria of the MTBc.

The label may comprise a detectable label such as a radiolabel, fluorescent molecule, enzymatic marker or chromogenic marker—eg. a dye that produces a visible colour change upon hybridisation of the probe. By way of example, the label may be digoxygenin, fluorescein-isothiocyanate (FITC) or R-phycoerythrin. The label may be a reporter molecule, which is detected directly, such as by exposure to photographic or X-ray film. Alternatively, the label is not directly detectable, but may be detected indirectly, for example, in a two-phase system. An example of indirect label detection is binding of an antibody to the label.

In one embodiment, the probe comprises a tag. Hence, following hybridisation of tagged probe to amplification product, the tag is associated with the bound amplification product. Thus, in one embodiment, the assay comprises capturing the tag (preferably following removal of unbound probe) and correlating presence of the tag with presence of bound amplification product, and hence the presence of mycobacteria of the MTBc.

In one embodiment, the tag is captured using a capture molecule, which may be attached (eg. coated) onto a substrate or solid support, such as a membrane or magnetic bead.

Capture methods employing magnetic beads are advantageous because the beads (plus captured, tagged probe bound to amplification product) can easily be separated from the sample, using conventional techniques known in the art.

Examples of suitable tags include biotin and streptavidin. In this regard, a biotin tag may be captured using streptavidin, which may be coated onto a substrate or support such as a bead (for example a magnetic bead) or membrane. Likewise, a streptavidin tag may be captured using biotin, which may be coated onto a substrate or support such as a bead (for example a magnetic bead) or membrane. Other exemplary pairs of tags and capture molecules include receptor/ligand pairs and antibody/antigen (or hapten or epitope) pairs.

Thus, in one embodiment, the probe is tagged with biotin, and the detection step comprises contacting the sample with a streptavidin-coated magnetic bead, which captures the biotin-tagged probe bound to amplification product. The magnetic bead (plus captured, tagged probe bound to amplification product) is then separated from the sample, thereby separating the amplification product from the sample. The amplification product can then be detected by any known means.

In one aspect, the probe is immobilised onto a support or platform. Immobilising the probe provides a physical location for the probe, and may serve to fix the probe at a desired location and/or facilitate recovery or separation of probe. The support may be a rigid solid support made from, for example, glass or plastic, such as a bead (for example a magnetic bead). Alternatively, the support may be a membrane, such as nylon or nitrocellulose membrane. 3D matrices are also suitable supports for use with the present invention—eg. polyacrylamide or PEG gels.

Immobilisation to a support/platform may be achieved by a variety of conventional means. By way of example, immobilisation onto a support such as a nylon membrane may be achieved by UV cross-linking. Biotin-labelled molecules (eg. probes) may be bound to streptavidin-coated substrates (and vice-versa), and molecules prepared with amino linkers may be immobilised onto silanised surfaces. Another means of immobilising a probe is via a poly-T tail or a poly-C tail, for example at the 3' or 5' end.

In one embodiment, the probe hybridises to the amplification product but does not hybridise to the sequence of primer-primer dimers. In an alternative embodiment, the probe hybridises to primer-primer dimers, but with a lower binding affinity as compared with the binding affinity of the probe for the amplification product.

In one embodiment, the target nucleic acid sequence to which the probe hybridises within the amplification product is not present in the sequence of the primer dimer. In an alternative embodiment, the target nucleic acid sequence to which the probe hybridises within the amplification product is present in the sequence of the primer dimer, but is poorly accessible, preferably inaccessible, to the probe.

Thus, in one embodiment, hybridisation of the probe enables amplification product to be distinguished from primer dimer.

In one embodiment, the target nucleic acid sequence to which the probe hybridises within the amplification product comprises (or consists of) the nucleotide sequence located between the target nucleic acid sequences to which the forward and reverse primers hybridise. This target nucleic acid sequence is preferably not present (or is poorly accessible or inaccessible to the probe) in the sequence of the primer dimers. Hence, in one embodiment, the probe does not hybridise to primer dimer (or hybridises with lower affinity as compared with the amplification product).

In one embodiment, the target nucleic acid sequence to which the probe hybridises within the amplification product comprises a nucleotide sequence selected from GCGC, TCGC, GGGA, ATTC or TTGC.

In one aspect, the amplification product is a double-stranded nucleic acid molecule and is detected by a method comprising melt curve analysis. Melting curve analysis is an assessment of the dissociation-characteristics of double-stranded nucleic acid (eg. DNA) during heating. Melt curve analysis is illustrated in FIGS. 3, 4, 8 and 10-12. In one embodiment, the amplification product has a Tm in the range 90-95° C., preferably in the range 92-93° C., most preferably about 92.5° C.

Melt curve analysis can also be used to distinguish the amplification product from primer dimer. Thus, in one embodiment, the Tm of the primer dimer is different from the Tm of the amplification product. In one embodiment, the primer dimer has a Tm in the range 82-89° C., preferably in the range 84-88° C., most preferably about 86° C.

In one aspect, the amplification product is detected by a method comprising contacting the sample with an enzyme (such as a restriction endonuclease) that digests the amplification product, and identification of digestion products.

In this aspect, the restriction endonuclease recognises a restriction site that is located within the sequence of the amplification product.

Restriction endonuclease digestion can also be used to distinguish the amplification product from primer dimer. In one embodiment, the restriction endonuclease digests the amplification product but does not digest the primer dimer. In one embodiment, the restriction endonuclease recognises a restriction site that is located within the sequence of the amplification product but is not present in the sequence of the primer dimer. Alternatively, the restriction site is located within the sequence of the primer dimer, but is poorly accessible or inaccessible to the restriction endonuclease.

In one embodiment, the restriction site within the amplification product is located between the target nucleic acid sequences to which the forward and reverse primers hybridise. This nucleic acid sequence is preferably not present (or is poorly accessible or inaccessible to the restriction endonuclease) in the sequence of the primer dimers.

In one embodiment, the restriction endonuclease recognises and cleaves a target sequence selected from GCGC, TCGC, GCGA, CTTC, GAAG, GCAA, TTGC, CUT or AAAG. In one embodiment, the restriction endonuclease is HhaI.

Thus, in one embodiment, the restriction endonuclease digests the amplification product but does not digest the primer dimer. In this embodiment, the presence of digestion products confirms that amplification product is present and hence confirms the presence of MTBc mycobacteria. In contrast, the absence of digestion products confirms that amplification product is absent, and hence confirms the absence of MTBc mycobacteria.

In an alternative embodiment, the restriction endonuclease digests both the amplification product and the primer dimer, but at different positions. In this embodiment, the restriction site for the restriction endonuclease is present in both the amplification product and the primer dimer, but at different positions. Hence, the digestion products of the amplification product and the digestion products of the primer dimer are different and may be distinguished from each other.

The digestion products may be detected by any known means, for example by a method comprising any of the detection techniques discussed above.

In one embodiment, the digestion products of the amplification product are detected (and/or distinguished from the primer dimers, or digestion products thereof) by virtue of their size, for example by a method comprising gel electrophoresis.

In one embodiment, the digestion products of the amplification product are in the range of 15-27 nucleotides long, preferably at least 16, 17, 18, 19 or 20 nucleotides long and preferably up to 26, 25 or 24 nucleotides long.

Preferably, the digestion products are in the range of 20-25 nucleotides long, and more preferably about 21, 22 or 23 nucleotides long.

The method of the present invention enables quantitative estimates of mycobacterial load to be determined. Determining MTBc mycobacterial load has many useful applications, such as for clinical guidance and for determining therapy, for patient management and for assessing vaccine efficacy.

In one aspect, measuring the amount of amplification product detected enables quantification of the amount of MTBc nucleic acid in a sample.

In one embodiment, the amplification product is labelled and the amount of amplification product is measured by detecting the label and measuring the amount of label. In one embodiment, the amplification product is tagged and the amount of amplification product is quantified by capturing the tag and measuring the amount of captured tag.

In one embodiment, the amplification product is hybridised with an oligonucleotide probe, and the amount amplification product is measured by measuring the amount of probe-amplification product hybridisation complexes. In one embodiment, the probe is tagged or labelled, and the amount of probe-amplification product hybridisation complexes is measured by detecting the label or capturing the tag, and measuring the amount of label or captured tag.

In one embodiment, the amplification product is digested with a restriction endonuclease, and the amount of amplification product is measured by detecting digestion products of the amplification product, and measuring the amount of digestion product.

Thus, in one aspect, the present invention provides an in vitro method for quantitating MTBc mycobacterial load (eg. *M. tuberculosis* load or *M. Bovis* load) in a sample of interest, comprising: (a) carrying out a detection method according to the present invention on said sample of interest; and (b) carrying out said method on a test sample of predetermined known MTB mycobacterial load; and (c) comparing the amount of amplification product detected from the sample of interest with the amount of amplification product detected from the test sample; and thereby quantitating MTBc mycobacterial load in the sample of interest.

In another aspect, the method of the present invention is useful for determining efficacy of a course of treatment for MTBc mycobacteria such as *M. tuberculosis* or *M. bovis* over a period of time, for example a course of drug therapy, such as vaccine therapy.

Thus, in one aspect, the present invention provides an in vitro method of determining the efficacy of an anti-MTBc mycobacterial drug (such as an anti-*M. tuberculosis* drug or an anti-*M. bovis* drug) over the course of a period of drug therapy, comprising: (a) carrying out a detection method according to the present invention on a first sample obtained at a first time point within or prior to the period of drug therapy; (b) carrying out said method on one or more samples obtained at one or more later time points within or after the period of drug therapy; and (c) comparing the amount of amplification product detected from the first sample with the amount of amplification product detected from the one or more later samples; and thereby determining drug efficacy over the course of the period of drug therapy.

In one embodiment, a reduction in the quantity of amplification product detected from the one or more later samples, as compared with the quantity of amplification product detected from the first sample, indicates efficacy of the drug against MTBc mycobacteria.

In another aspect, the present invention is useful for determining the efficacy of a vaccine against infection with MTBc mycobacteria such as *M. tuberculosis* or *M. bovis*.

Thus, in one aspect, the present invention provides an in vitro method of determining the efficacy of a vaccine against MTBc mycobacteria, comprising: (a) carrying out a detection method according to the present invention on a first sample obtained from a patient at a first time point prior to vaccination; (b) carrying out said method on a sample obtained from said patient at one or more later time points after vaccination and following challenge with MTBc mycobacteria; and (c) comparing the amount of amplification product detected from the first sample with the amount of amplification product detected from the one or more later samples; and thereby determining vaccine efficacy.

In one embodiment, a reduction in the quantity of amplification product detected from the one or more later samples, as compared with the quantity of amplification product detected from the first sample, indicates efficacy of the vaccine against MTBc mycobacterial infection (eg. *M. tuberculosis* infection or *M. bovis* infection).

The invention also provides reagents such as forward primers, reverse primers, probes, combinations thereof, and kits comprising said reagents, for use in the above-described methods of the present invention.

In one embodiment, the sequence of the forward and/or reverse oligonucleotide primer does not comprise or consist of the entire nucleic acid sequence of a full length MIRU repeat element, or the complement thereof.

In one aspect, the invention provides a forward oligonucleotide primer that hybridises to a target nucleic acid sequence located within a MIRU repeat element. In one embodiment, said target nucleic acid sequence comprises (or consists of) a nucleotide sequence that is at least 90% identical to (preferably 91, 92, 93, 94, 95, 96, 97, 98, 99 or 100% identical to) the complement of a nucleotide sequence selected from SEQ ID NOs: 25-39, or a fragment thereof as defined above. In one embodiment, said target nucleic acid sequence is specific to mycobacteria of the MTB complex.

In one embodiment, the forward primer comprises (or consists of) a nucleotide sequence having at least 80% identity to (preferably 81, 82, 83, 84, 85, 86, 87, 88, 89, 90, 91, 92, 93, 94, 95, 96, 97, 98, 99 or 100% identity to) a nucleotide sequence selected from SEQ ID NOs: 47 or 48.

In one embodiment, the forward primer comprises (or consists of) a fragment of SEQ ID NOs: 47 or 48 (or a sequence variant thereof as defined above) wherein said fragment comprises at least 15 consecutive nucleotides thereof. Preferably said fragment comprises at least 16, 17, 18, 19, 20 or 21 consecutive nucleotides thereof.

In one aspect, the invention provides a reverse oligonucleotide primer that hybridises to a target nucleic acid sequence located within a MIRU repeat element. In one embodiment, said target nucleic acid sequence comprises (or consists of) a nucleotide sequence that is at least 90% identical to (preferably 91, 92, 93, 94, 95, 96, 97, 98, 99 or 100% identical to) a nucleotide sequence selected from SEQ ID NOs: 40-46. In one embodiment, said target nucleic acid sequence is specific to mycobacteria of the MTB complex.

In one embodiment, the reverse primer comprises (or consists of) a nucleotide sequence having at least 80% identity to (preferably 81, 82, 83, 84, 85, 86, 87, 88, 89, 90, 91, 92, 93, 94, 95, 96, 97, 98, 99 or 100% identity to) a nucleotide sequence selected from SEQ ID NOs: 49-51, or a fragment thereof as defined above.

In one embodiment, the reverse primer comprises (or consists of) a fragment of SEQ ID NO: 49, 50 or 51 (or a sequence variant thereof as defined above) wherein said fragment comprises at least 15 consecutive nucleotides thereof. Preferably said fragment comprises at least 16, 17, 18 or 19 consecutive nucleotides thereof.

In one embodiment, the forward primer and/or the reverse primer comprise a tag or label, as described above.

The present invention further provides a pair of forward and reverse oligonucleotide primers, comprising a forward primer as defined above and a reverse primer as defined above.

The present invention also provides a kit for detecting mycobacteria belonging to the MTB complex in a sample, comprising a pair of forward and reverse oligonucleotide primers as defined above. The kit optionally comprises reagents for amplification of an MTB complex-specific nucleic acid sequence. The kit optionally comprises reagents for detection of the amplification product.

In one embodiment, reagents for detection of the amplification product comprise an oligonucleotide probe as described above, which hybridises to said amplification product.

In one embodiment, the sequence of the oligonucleotide probe does not comprise or consist of the entire nucleic acid sequence of a full length MIRU repeat element, or the complement thereof.

In one embodiment, said probe comprises (or consists of) a nucleotide sequence having at least 80% identity to (preferably at least 85, 90, 95 or 100% identity to) a nucleotide sequence selected from SEQ ID NOs: 52-57, or a fragment thereof having at least 8 or 9 consecutive nucleotides thereof.

In one embodiment, the probe comprises a tag or label, as described above.

In one embodiment, reagents for detection of the amplification product comprise an enzyme such as a restriction endonuclease (such as HhaI) that digests the amplification product, as described above.

The present invention is discussed in more detail by means of the Examples described below, and by the Figures.

FIG. 1 illustrates the amplification of up to 5 adjacent MIRU repeat elements at the same MIRU locus, detailing the multiple forward and reverse primer target sequences and the formation of an amplification product comprising nucleic acid sequence that spans up to 5 adjacent MIRU repeat elements.

FIG. 2 illustrates the generation of an amplification product comprising a concatenation of nucleic acid sequences from multiple MIRU repeat elements.

Figure 3:
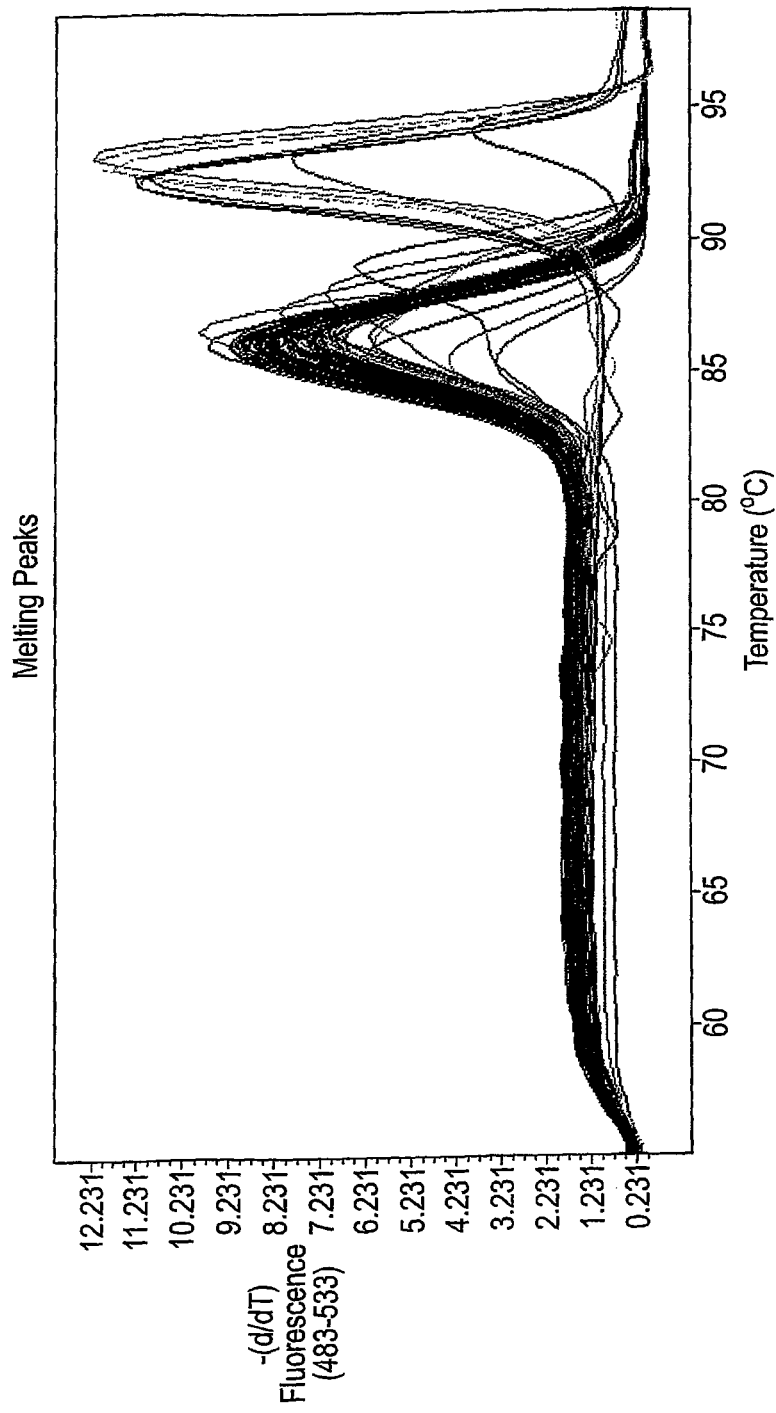
Figure 4:
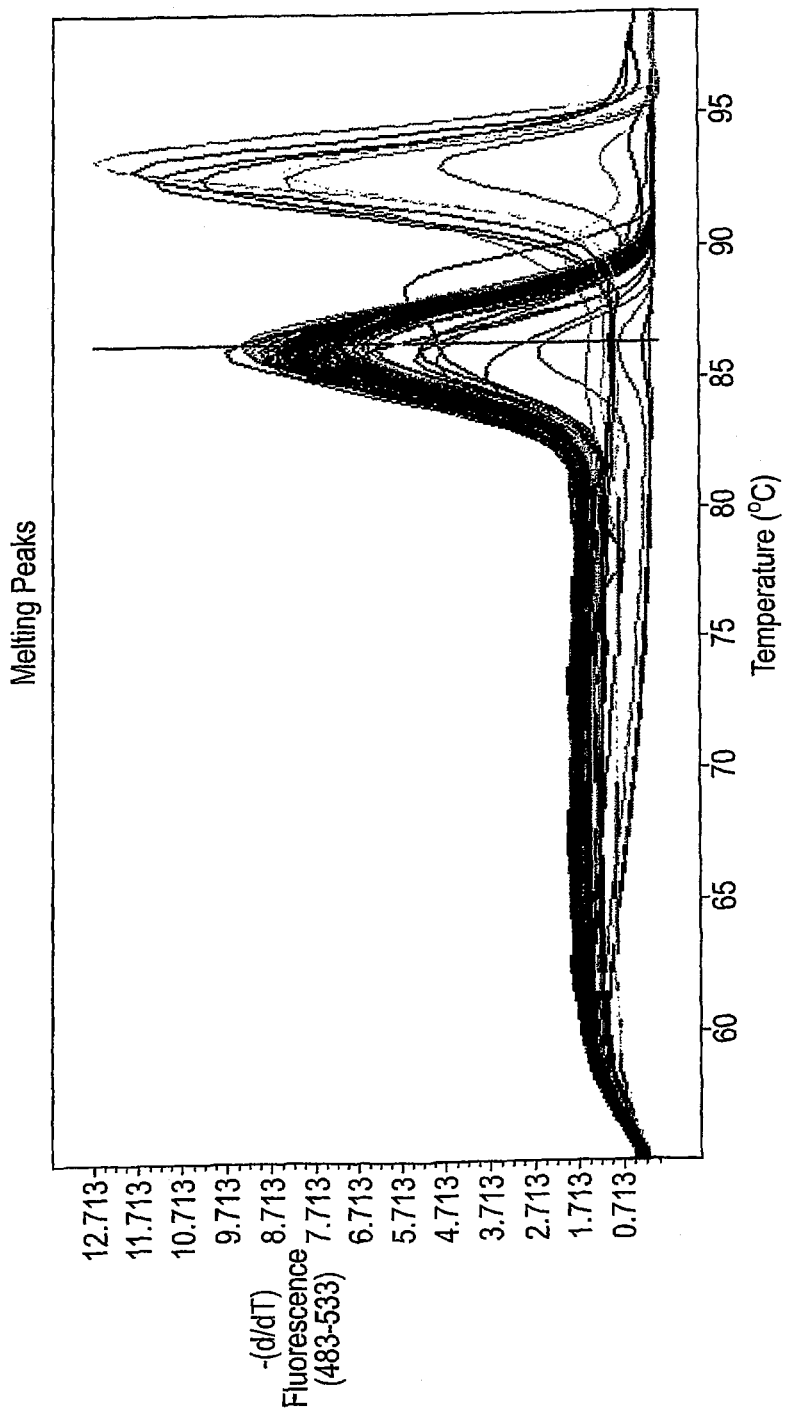

FIGS. 3 and 4 illustrate melt curves. Fluorescence is measured against melt temperature (Tm). Negative samples=86° C. melt, Positive samples=92° C. melt. FIG. 3 is a melt curve from a low microscopy sample (about 30-1000 bacteria per ml of sputum), with 8 positive melts.

Figure 5:
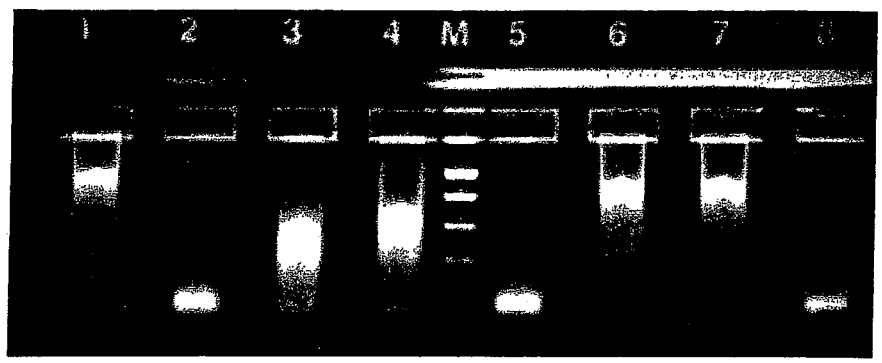

FIG. 5 illustrates agarose gel analysis of real-time PCR generated products. Lane 7 illustrates a concatamer of about 11 Kb. The key is as follows:

| | Lane | | | | | | | |
|---|---|---|---|---|---|---|---|---|
| | 1 Neat | 2 $10^{-6}$ | 3 $10^{-5}$ | 4 $10^{-4}$ | 5 Neg | 6 $10^{-2}$ | 7 $10^{-1}$ | 8 Neg |
| Tm | 92.6 | 86.5 | 92.9 | 93.2 | 86.2 | 92.6 | 92.6 | 86.11 |
| Ct | 16.7 | 34.6 | 33.2 | 30.1 | 36.0 | 23.7 | 20.3 | 35.1 |

Figure 6:
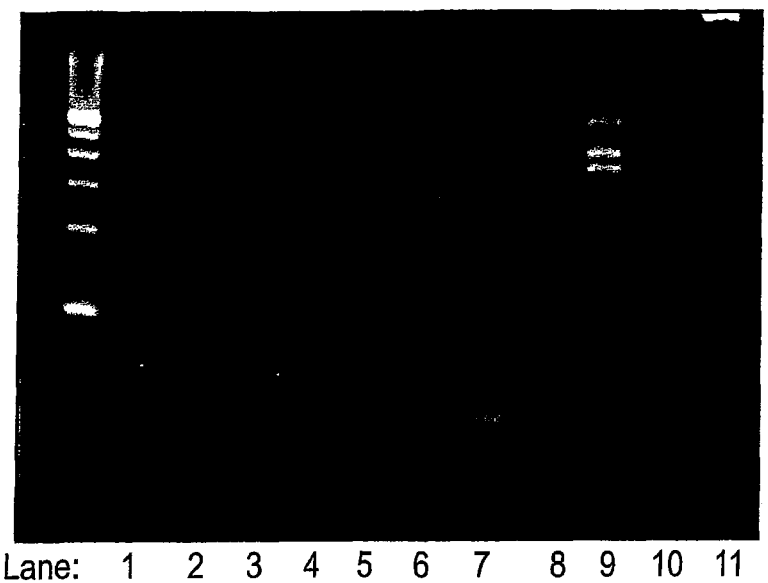
Figure 7:
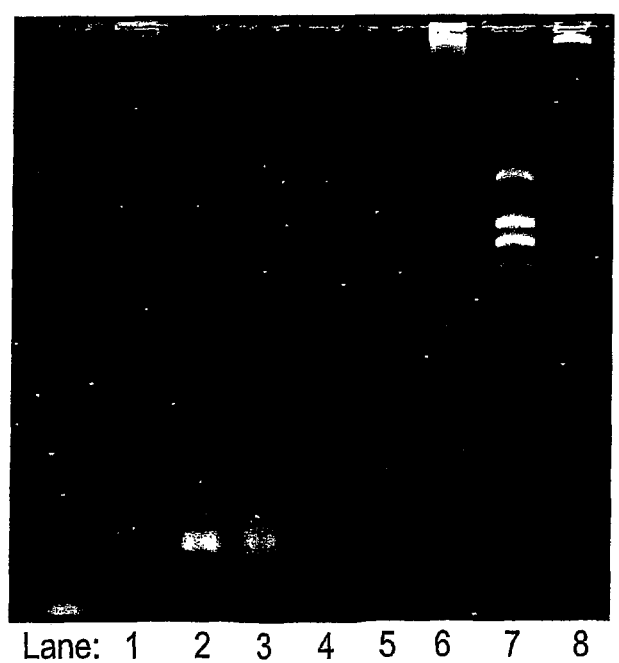
Figure 8:
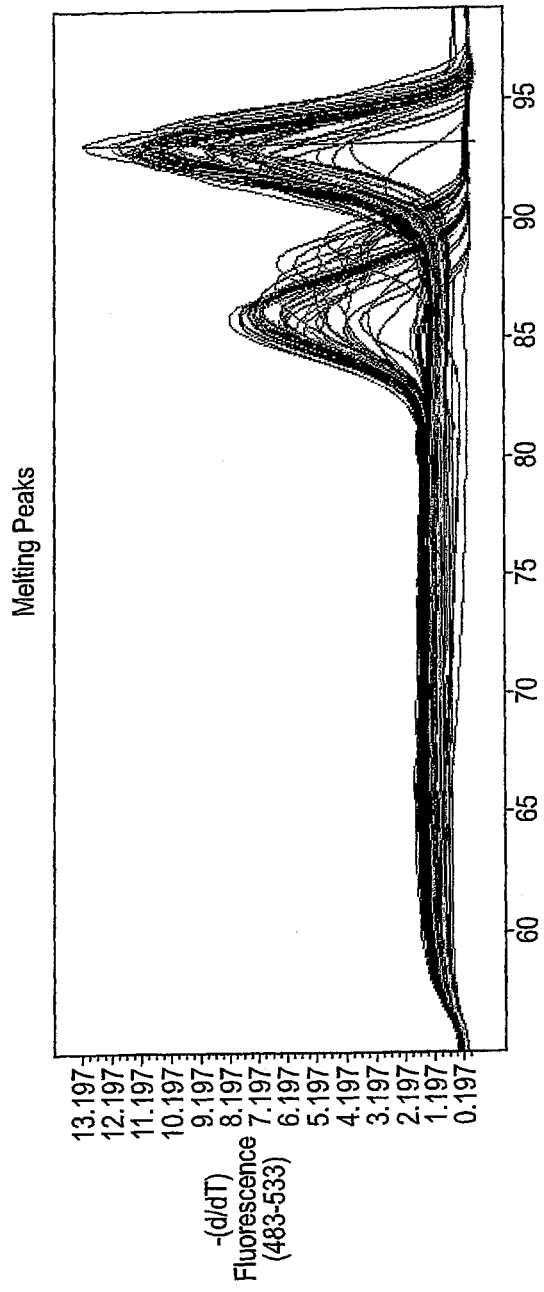
Figure 8:
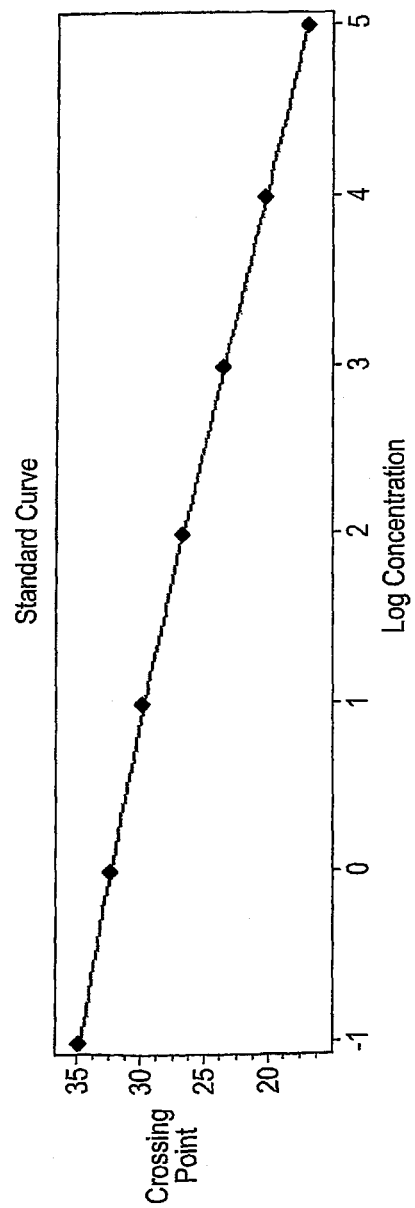

FIG. 6 illustrates digestion of (Block-based) sputum amplicons. The key is as follows:
Lane 1=Sputum a: 1-10 rods Tb
Lane 2=Sputum b: >90 rods Tb
Lane 3=Sputum c: >90 rods Tb
Lane 4=Sputum d: 1-10 rods Tb
Lane 5=*M. malmoense* (1-10 rods)
Lane 6=*M. chelonae* (10-90 rods)
Lane 7=H37R DNA
Lane 8=Neg
Lane 9=Digested PGem
Lane 10=Sputum b, undigested
Lane 11=PGem undigested FIG. 7 illustrates digestion of sputum amplicons. The key is as follows:
Lane 1=Sputum 6444
Lane 2=Sputum b
Lane 3=Sputum c
Lane 4=Sputum d
Lane 5=Neg (primer dimer)
Lane 6=Undigested 6444
Lane 7=Pgem digested
Lane 8=PGem undigested FIG. 8 illustrates melting peak and amplification curve data for a low positive microscopy sputum sample (plate comprises 50% Neg, 50% Pos): 72° C. annealing for 1 second, ramp rate 1° C./s, (no extension).

Figure 9:
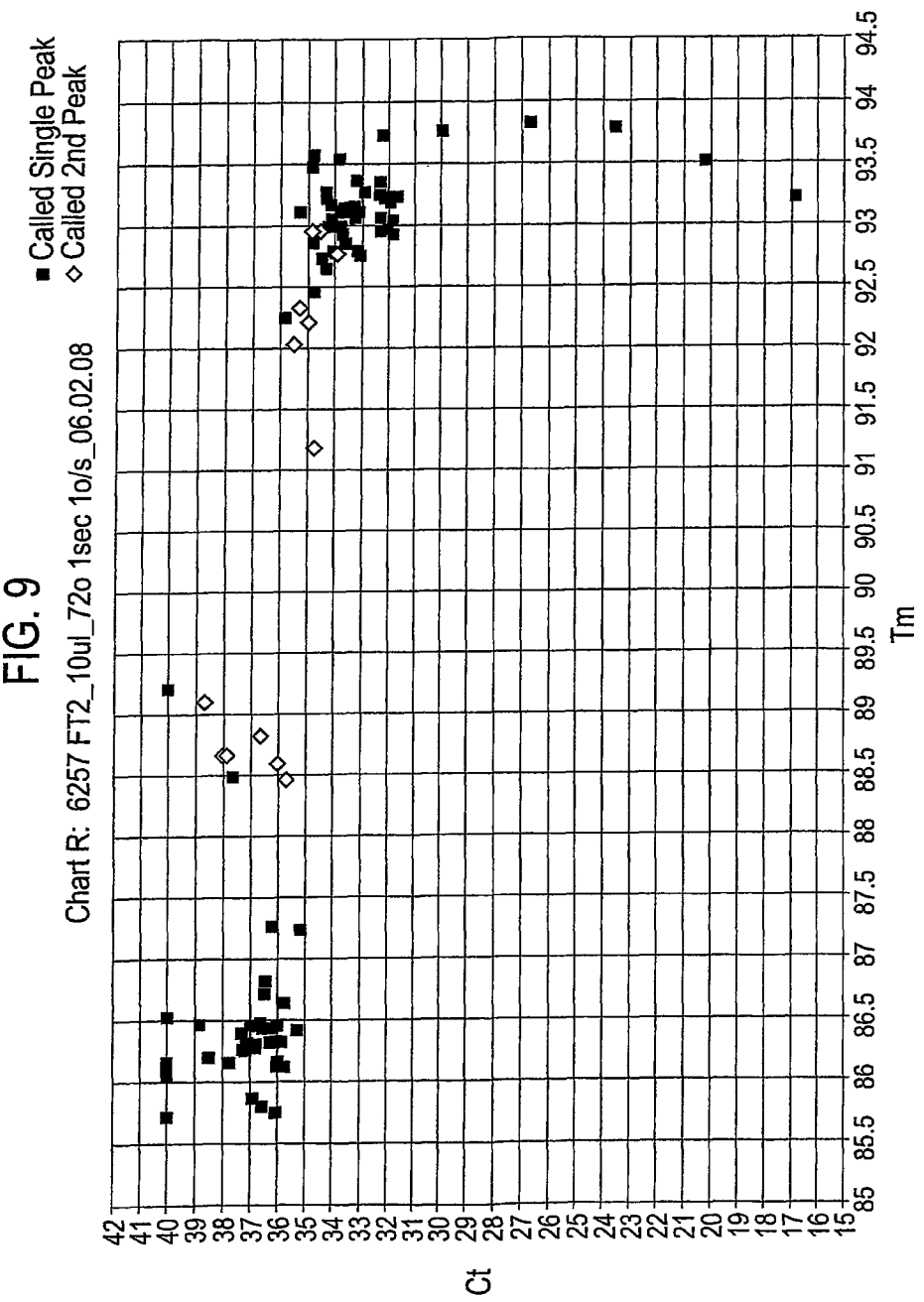

FIG. 9 illustrates the Ct (the cycle number at which the product starts to accumulate in sufficient amounts to be detected) against Tm.

Figure 10:
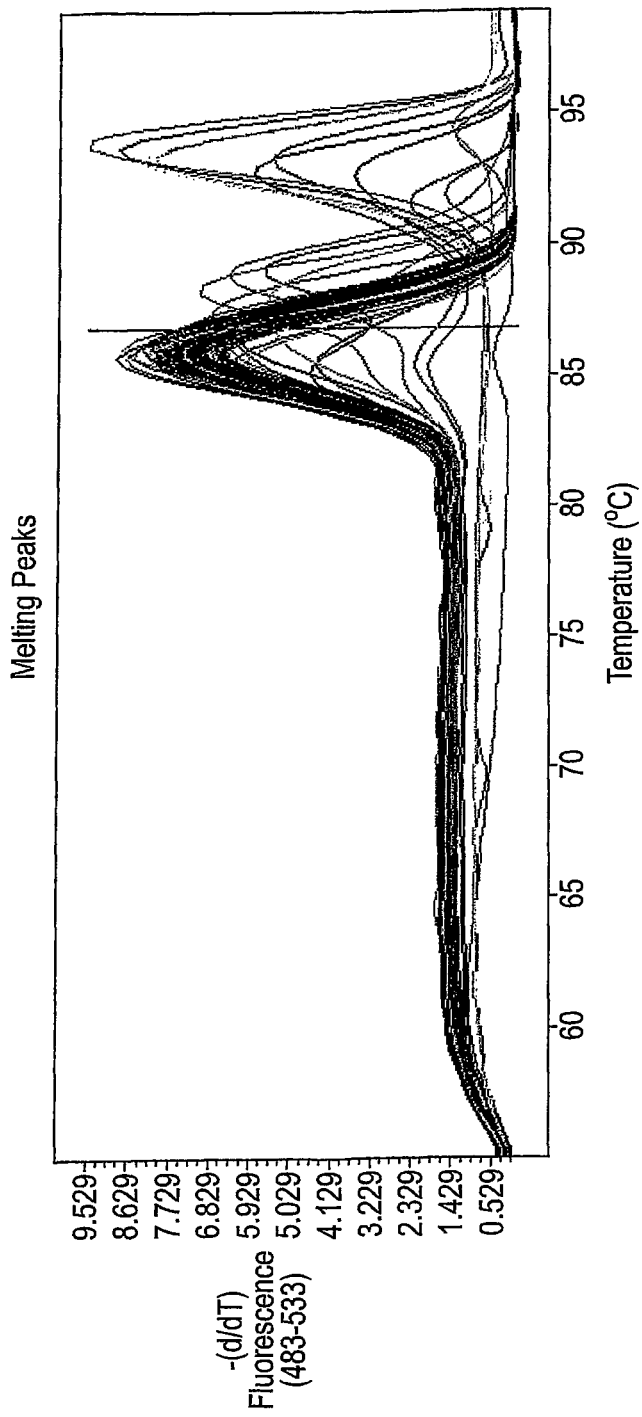
Figure 11:
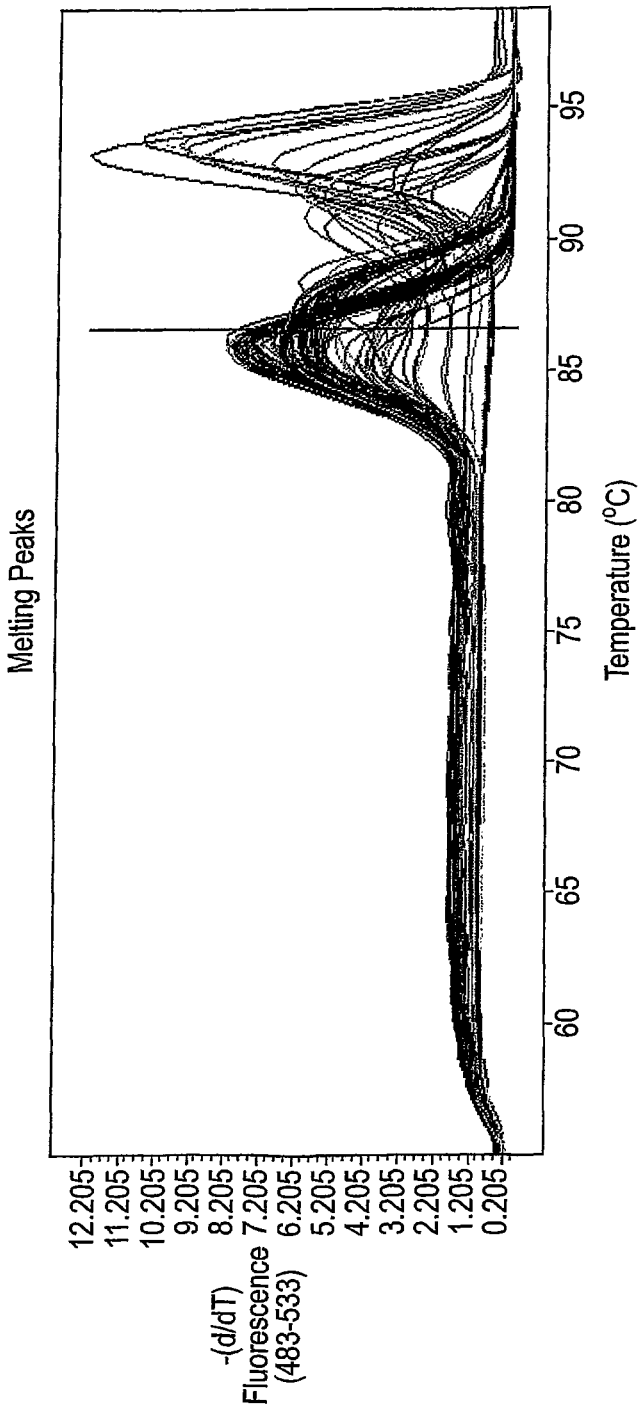
Figure 12:
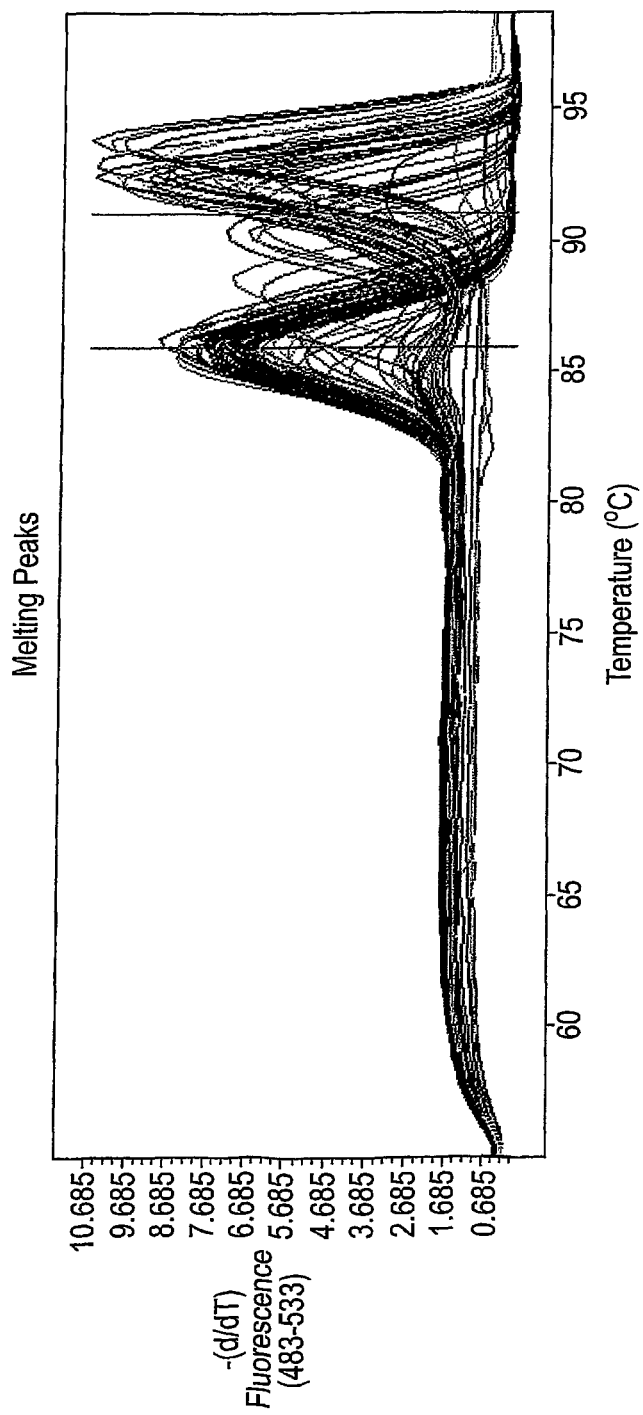

FIGS. 10, 11 and 12 illustrate melt curves obtained from low microscopy positive sputa in 3 separate assays.

Figure 13:
Figure 14:
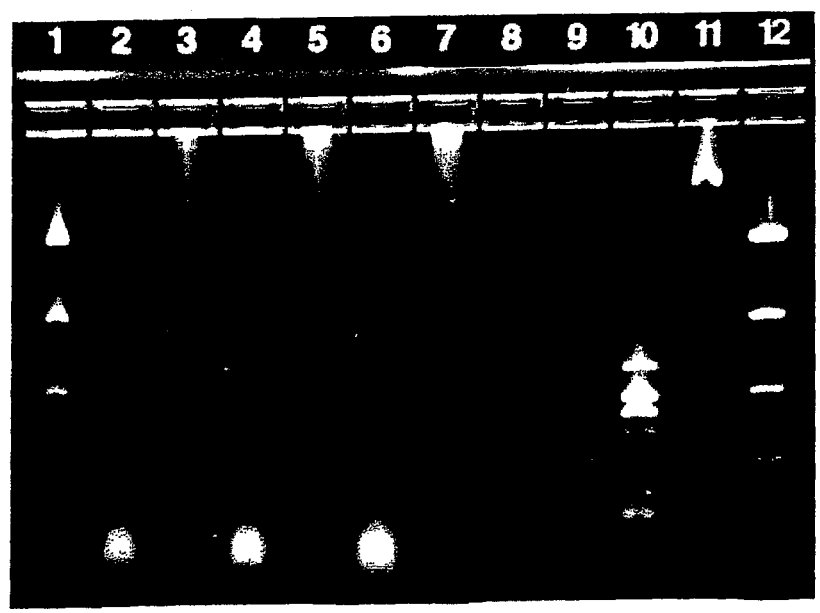
Figure 15:
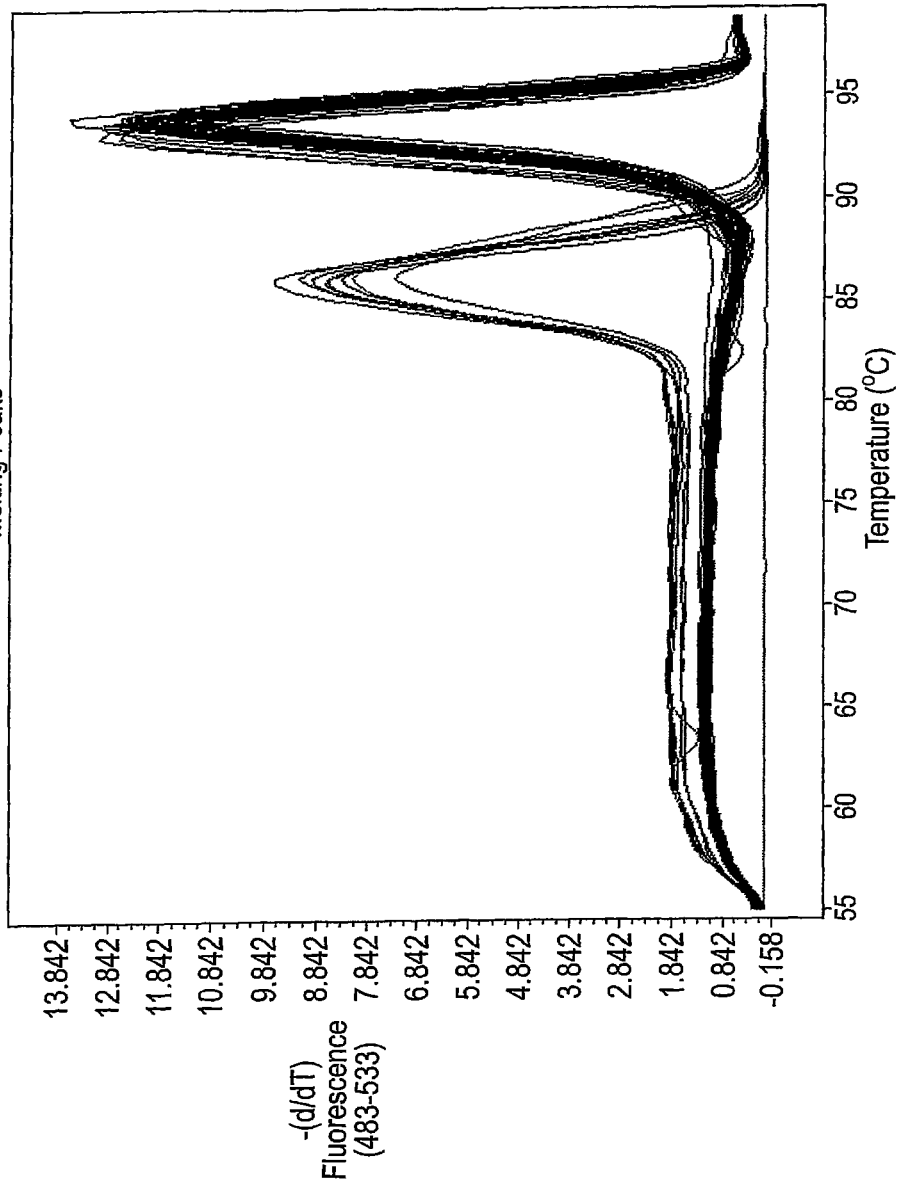

FIG. 13 illustrates electrophoresis of *M. bovis* PCR products. The key is as follows:
Lane 1: Low molecular weight ladder
Lane 2: *M. bovis* '62'
Lane 3: *M. bovis* '64'
Lane 4: *M. bovis* '65'
Lane 5: Negative Control
Lane 6: Mtb Positive control
Lane 7: Low molecular weight ladder FIG. 14 illustrates restriction endonuclease digestion of *M. bovis* products. The key is as follows:
Lane 1: Low molecular weight ladder
Lane 2: *M. bovis* '62' digested
Lane 3: *M. bovis* '62' un-digested
Lane 4: *M. bovis* '64' digested
Lane 5: *M. bovis* '64' un-digested
Lane 6: *M. bovis* '65' digested
Lane 7: *M. bovis* '65' un-digested
Lane 8: Neg control digested
Lane 9: Neg control un-digested
Lane 10: Pgem vector control digested
Lane 11: Pgem vector control un-digested
Lane 12: Low molecular weight ladder FIG. 15 illustrates Melting Curves showing all negative controls with a Tm of ~86° C. and all *M. bovis* samples with a positive Tm of ~93.5° C.

Figure 16:
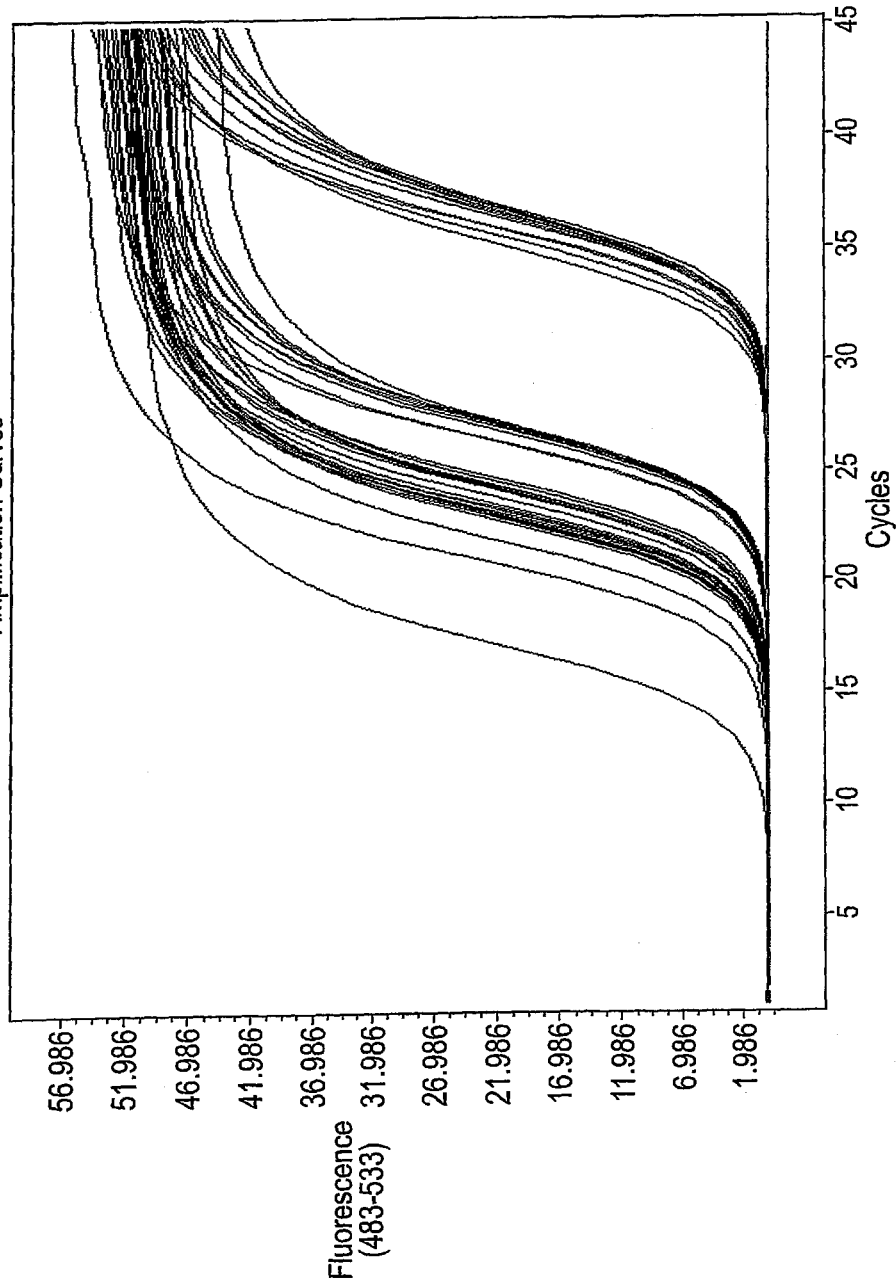

FIG. 16 illustrates the melt curve data for the *M. bovis* panel in a different format and indicates the ct (the cycle number at which the product starts to accumulate in sufficient amounts to be detected).

EXAMPLES

Example 1

*M. Tuberculosis*: Amplification

Sputum samples were kindly donated from both the Newcastle Regional HPA laboratory, and the Royal London Hospital, UK.

The national standard operating procedure protocol was used to process the sputum. All samples were processed within a Class I cabinet in a category III laboratory. 1 ml of sputum was heated to 105° C. for 10 min, and the outside of the tube disinfected prior to removal from the laboratory.

The following primers were synthesised from MWGEurofins Ltd.:

```
Mtb det Reverse:              (SEQ ID NO: 49)
5' CGC CGG CGA CGA TGC AGA GC 3'

Mtb det Forward:              (SEQ ID NO: 47)
5' GGC GCC GCT CCT CCT CAT CGC T 3'
```

Block-Based Method:

PCR reaction mixtures consisted of 25 μl ReadyMix™ (final concentrations: 1.5U Taq polymerase, 10 mM tris-HCl, 50 mM KCl, 1.5 mM MgCl2, 0.2 mM dNTPs) (Sigma, UK), 5 pmol reverse primer, 5 pmol forward primer (MWGEurofins, UK), 200 ng template DNA or 1 μl of inactivated sputum, and nuclease free water to total of 50 μl.

PCR cycling parameters on the Applied Biosystems 9700 thermal cycler were as follows: 95° C. for 12 min followed by 45 cycles of 94° C. for 30 sec, 64° C. for 1 min, and 72° C. for 2 min.

Real-Time Method:

PCR reaction mixtures consisted of 10 μl 2× Lightcycler 480® SYBR green I mastermix (containing FastStart Taq polymerase, dNTP mix, SYBR green I dye, and 3.5 mM $MgCl_2$), 0.5 μM both forward and reverse primers, 5 μl of template DNA and nuclease free water to total of 20 μl.

PCR cycling parameters on the Roche Lightcycler 480 (LC480) were as follows: 95° C. for 12 min followed by 45 cycles of 95° C. for 10 sec, 64° C. for 1 sec, and 72° C. for 1 min. The ramping rates were 4.4, 2.2, and 4.4° C./s respectively.

Alternative PCT cycling parameters do not include a separate annealing temperature: after an initial denaturation at 95° C. for 12 mins (4.4° C./s ramp), the Real-time cycling parameters are 45 cycles of 95° C. for 10 seconds, 72° C. for one second; with ramping rates of 1° C. per second.

Example 2

*M. Tuberculosis*: Analysis of PCR Product

Block-Based Analysis

PCR products were analysed by electrophoresis (65V for 120 min) in 1.5% (w/v) agarose gels (Invitrogen, UK). Gels were stained for 30 min with 20 μl of SYBR green I nucleic acid gel stain (10,000×; Sigma Aldrich, UK) in 200 ml of 1×TBE buffer (Invitrogen) and visualised by ultra violet irradiation (BioRad).

Due to the nature of the repeat element, the primers yielded an amplification product that forms a large non-specific smear on the gel.

As illustrated in FIG. 1, amplification products may be derived from a single MIRU repeat element (if both primers bind within the same repeat element), in which case the amplification product is about 44 bp.

Alternatively, the amplification products may be derived from several adjacent MIRU repeat elements within the same locus, in which case the amplification product may be about 680 bp (for a locus with 13 copies of the element).

However, evidence exists of the amplification of much larger products/concatemers as judged by agarose gel electrophoresis. It is hypothesised that the early products in the reaction are acting as additional primers allowing the formation of much larger products (>12 Kb), as illustrated diagrammatically in FIG. 2.

As such, the products were further characterised by a variety of methods.

Turning to FIG. 5, the gel picture shows a concatamer of over 11 Kb. Following digestion with HhaI, this huge product is broken down into the predicted small fragments—see FIGS. 6 and 7.

Negative samples (primer dimers) formed a band of approximately 40 bp in size. Product size was determined by direct comparison with a 1 Kb ladder (Promega, UK).

Real-Time Analysis

Amplification curves were analysed by the Absolute Quantification/$2^{nd}$ Derivative Max method derived from the LC480 software. Melt curve analysis was automatically performed using the Negative first derivative (−dF/dT) method within the LC480 software.

The melt curve protocol is: 99° C. for 10 sec, 55° C. for 20 sec, and finally reheating to 99° C., with 5 data acquisitions per ° C. The ramping rates were 4.4 and 2.2° C./s respectively.

The results illustrated in FIGS. 3, 4, 8 and 10-12 are from different sputum samples. The results show that the negatives (primer dimers) melt at around 86° C., whereas the amplification product melts at around 91° C.

The chart in FIG. 9 represents the melt curve data in a different format and indicates the ct (the cycle number at which the product starts to accumulate in sufficient amounts to be detected).

Example 3

*Mycobacterium Bovis*: Amplification

Approximately 200 ng extracted *Mycobacterium bovis* DNA was used as template in following real-time PCR.

The following primers were synthesised from MWGEurofins Ltd.:

```
Mtb det Reverse:                    (SEQ ID NO: 49)
5' CGC CGG CGA CGA TGC AGA GC 3'

Mtb det Forward:                    (SEQ ID NO: 47)
5' GGC GCC GCT CCT CCT CAT CGC T 3'
```

Real-Time Method:

PCR reaction mixtures consisted of 10 μl 2× Lightcycler 480® SYBR green I mastermix (containing FastStart Taq polymerase, dNTP mix, SYBR green I dye, and 3.5 mM $MgCl_2$), 0.5 μM both forward and reverse primers, 200 ng of template DNA and nuclease free water to total of 20 μl.

The alternative PCR cycling parameters used on the Roche Lightcycler 480 (LC480) were as follows: 95° C. for 12 min followed by 45 cycles of 95° C. for 10 sec, and 72° C. for 1 sec. The ramping rates were 4.4, and 1.0° C./s respectively.

Example 4

*Mycobacterium Bovis*: Analysis of PCR Product

PCR products were analysed by electrophoresis (65V for 30 min) in 2.0% EGel (Invitrogen, UK). Gels were visualised by ultra violet irradiation (BioRad).

Negative samples (primer dimers) formed a band of approximately 40 bp in size.

Due to the nature of the repeat element, the primers yielded an amplification product that forms a large non-specific smear on the gel (see FIG. 13).

Amplification products appear as large concatemers as judged by agarose gel electrophoresis. It is hypothesised that the early products in the reaction are acting as additional primers allowing the formation of much larger products (>12 Kb).

The PCR products were further characterised by a variety of methods. Turning to FIG. 14, the gel picture shows each undigested *M. bovis* PCR product as a concatemer of over 11 Kb. Following digestion with HhaI, this huge product is broken down into the predicted small fragments.

Real-Time Analysis

Amplification curves were analysed by the Absolute Quantification/$2^{nd}$ Derivative Max method derived from the LC480 software. Melt curve analysis was automatically performed using the Negative first derivative (−dF/dT) method within the LC480 software.

The melt curve protocol is: 99° C. for 10 sec, 55° C. for 20 sec, and finally reheating to 99° C., with 5 data acquisitions per ° C. The ramping rates were 4.4 and 2.2° C./s respectively.

The results illustrated in FIG. 15 are from *M. bovis* samples. They show that the negatives (primer dimers) melt at around 86° C., whereas the amplification product melts at around 93.5° C.

The results illustrated in FIG. 15 are shown below as individual melting temperatures:

Tm (melting temperature) calling for *M. bovis* panel

| Pos | Name Tm1 | Tm2 |
|---|---|---|
| A1 | *M bovis* 62 | 93.74 |
| A2 | *M bovis* 62 | 94.23 |
| A3 | *M bovis* 64 | 93.63 |
| A4 | *M bovis* 65 | 93.65 |
| A5 | *M bovis* 65 NEAT | 93.10 |
| A6 | Mtb POS CONTROL | 93.11 |
| B1 | *M bovis* 62 | 93.58 |
| B2 | *M bovis* 62 | 93.47 |
| B3 | *M bovis* 64 | 93.57 |
| B4 | *M bovis* 65 | 93.45 |
| B5 | NEG CONTROL | 85.96 |
| B6 | Mtb POS CONTROL | 93.79 |
| C1 | *M bovis* 62 | 93.63 |
| C2 | *M bovis* 64 | 93.62 |
| C3 | *M bovis* 64 | 93.24 |
| C4 | *M bovis* 65 | 93.51 |
| C5 | NEG CONTROL | 85.76 |
| D1 | *M bovis* 62 | 93.69 |
| D2 | *M bovis* 64 | 93.23 |
| D3 | *M bovis* 64 | 86.19 |
| D4 | *M bovis* 65 | 93.54 |
| D5 | NEG CONTROL | 85.92 |
| E1 | *M bovis* 62 | 93.59 |
| E2 | *M bovis* 64 | 93.97 |

-continued

Tm (melting temperature) calling for *M. bovis* panel

| Pos | Name Tm1 | Tm2 |
|---|---|---|
| E3 | *M bovis* 65 | 93.72 |
| E4 | *M bovis* 65 | 93.85 |
| E5 | NEG CONTROL | 85.89 |
| F1 | *M bovis* 62 | 93.56 |
| F2 | *M bovis* 64 | 93.20 |
| F3 | *M bovis* 65 | 93.48 |
| F4 | *M bovis* 65 | 93.44 |
| F5 | NEG CONTROL | 85.85 |
| G1 | *M bovis* 62 | 93.63 |
| G2 | *M bovis* 64 | 93.10 |
| G3 | *M bovis* 65 | 93.36 |
| G4 | *M bovis* 62 NEAT | 92.94 |
| G5 | NEG CONTROL | 85.76 |
| H1 | *M bovis* 62 | 93.76 |
| H2 | *M bovis* 64 | 93.18 |
| H3 | *M bovis* 65 | 93.93 |
| H4 | *M bovis* 64 NEAT | N/A |
| H5 | NEG CONTROL | 86.10 |

The chart in FIG. 16 represents the melt curve data for the *M. bovis* panel in a different format and indicates the ct (the cycle number at which the product starts to accumulate in sufficient amounts to be detected).

REFERENCES

Dye C. et al. (2005) JAMA Vol. 293: 2767-2775.

Kamerbeek J. et al., (1997) J. Clin. Microbiol. Vol. 35: 907-914

Kent P. T. and Kubica G. P. (1985) Public health mycobacteriology: A guide for the level III laboratory. Atlanta: Department of Health and Human Services.

Poulet S. and Cole S. T. (1995) Arch. Microbiol., Vol. 163: 79-86.

Supply P. et al., J. Clin. Microbiol. Vol. 39, No. 10: 3563-3571

Thierry D. et al., J. Clin. Microbiol. Vol. 28, No. 12: 2668-2673

Yuen K. Y. et al. (1995) J Clin Pathol. Vol. 48(10): 924-928.

The invention claimed is:

1. A method for detecting nucleic acid of a *mycobacterium* belonging to the *Mycobacterium tuberculosis* (MTBc) in a sample, the method comprising:
  (a) contacting the sample with a pair of primers comprising a forward oligonucleotide primer and a reverse oligonucleotide primer, wherein said forward primer hybridizes to a target nucleic acid sequence that is located within multiple Mycobacterial Interspersed Repetitive Unit (MIRU) repeat elements, and wherein said reverse primer hybridizes to a target nucleic acid sequence that is located within the multiple MIRU repeat elements;
  wherein the forward primer comprises a sequence that is at least 95% identical to a nucleotide sequence selected from SEQ ID NOs: 25-39; and
  wherein the reverse primer comprises a sequence that is at least 95% identical to the complement of a nucleotide sequence selected from SEQ ID NOs: 40-46;
  (b) extending said forward and reverse primers to generate at least one amplification product; and
  (c) detecting the at least one amplification product.

2. The method according to claim 1, wherein said forward oligonucleotide primer is 18-30 nucleotides long.

3. The method according to claim 1, wherein said forward primer comprises a sequence that is selected from SEQ ID NOs: 25-39.

4. The method according to claim 1, wherein said reverse primer comprises a sequence that is identical to the complement of a nucleotide sequence selected from SEQ ID NOs: 40-46.

5. The method according to claim 1, wherein the at least one amplification product comprises a single amplification product formed by extension of the forward and reverse primers hybridized to the target nucleic acid sequences that are located within the same MIRU repeat element, and wherein said detection step comprises detecting the single amplification product.

6. The method according to claim 5, wherein the single amplification product is 30-55 nucleotides long.

7. The method according to claim 1, wherein said at least one amplification product comprises an amplification product formed by extension of the forward and reverse primers hybridized to target nucleic acid sequences that are located within different MIRU repeat elements within the same MIRU locus, and wherein said single amplification product comprises nucleic acid sequence from two or more adjacent MIRU repeat elements within the same MIRU locus, and wherein said detection step comprises detecting said single amplification product.

8. The method according to claim 1, wherein said forward primer and/or said reverse primer comprises a tag or label, wherein said tag or label is incorporated into the at least one amplification product during the primer extension step, and wherein the at least one amplification product is detected by a method comprising capturing the tag or detecting the label.

9. The method according to claim 1, wherein said forward primer and/or said reverse primer comprises a biotin tag; wherein said biotin tag is incorporated into the at least one amplification product during the primer extension step, and wherein the detection step comprises contacting the sample with a streptavidin-coated magnetic bead that captures the at least one biotin-tagged amplification product.

10. The method according to claim 1, wherein the detection step comprises:
  (i) contacting the sample with an oligonucleotide probe that forms a hybridization complex with the at least one amplification product, if present; and
  (ii) detecting the hybridization complex.

11. The method according to claim 10, wherein the oligonucleotide probe is 5-30 nucleotides long.

12. The method according to claim 10, wherein the oligonucleotide probe comprises a nucleotide sequence having at least 80% identity to a nucleotide sequence selected from SEQ ID NOs: 52-57, or a fragment thereof having at least 8 consecutive nucleotides thereof.

13. The method according to claim 10, wherein the oligonucleotide probe comprises a tag or label.

14. The method according to claim 1, wherein the detection step comprises melt curve analysis.

15. The method according to claim 1, wherein the detection step comprises:
  (i) contacting the sample with a restriction endonuclease that digests the at least one amplification product; and
  (ii) detecting digestion products of the at least one amplification product.

16. The method according to claim 15, wherein digestion products of the at least one amplification product are detected by a method comprising gel electrophoresis.

17. An in vitro method for quantitating a *Mycobacterium tuberculosis* complex (MTBc) mycobacterial load in a sample of interest, comprising:
  (a) carrying out the detection method of claim 1 on said sample of interest;
  (b) carrying out said detection method of claim 1 on a test sample of pre-determined known MTBc mycobacterial load; and (c) comparing the amount of the at least one amplification product detected from the sample of interest to the amount of the at least one amplification product detected from the test sample;

and thereby quantitating MTBc mycobacterial load in the sample of interest.

18. An in vitro method of determining efficacy of a drug against *Mycobacterium tuberculosis* complex (MTBc) mycobacteria, comprising:
(a) carrying out the detection method according to claim 1 on a first sample obtained at a first time point within or prior to a period of a treatment with the drug;
(b) carrying out the detection method of claim 1 on one or more samples obtained at one or more later time points within or after the period of the treatment; and
(c) comparing the amount of the at least one amplification product detected from the first sample with the amount of the at least one amplification product detected from the one or more later samples;

and thereby determining efficacy of the drug, wherein a reduction in the quantity of the at least one amplification product detected from the one or more later samples, as compared with the quantity of the at least one amplification product detected from the first sample, indicates efficacy of the drug against MTBc mycobacteria.

19. An in vitro method of determining the efficacy of a vaccine against a Mycobacteria tuberculosis complex (MTBc) mycobacterial infection, comprising:
(a) carrying out the detection method according to claim 1 on a first sample obtained from a patient at a first time point prior to vaccination;
(b) carrying out said detection method of claim 1 on a sample obtained from said patient at one or more later time points following vaccination and challenge with MTBc mycobacteria; and
(c) comparing the amount of the at least one amplification product detected from the first sample with the amount of the at least one amplification product detected from the one or more later samples;

and thereby determining vaccine efficacy, wherein a reduction in the quantity of the at least one amplification product detected from the one or more later samples, as compared with the quantity of the at least one amplification product detected from the first sample, indicates efficacy of the vaccine against the MTBc mycobacterial infection.

20. The method according to claim 5, wherein the single amplification product is 40-45 nucleotides long.

21. The method according to claim 5, wherein the single amplification product is about 44 nucleotides long.

22. The method according to claim 10, wherein the oligonucleotide probe is 8-12 nucleotides long.

23. The method according to claim 1, wherein:
(a) said forward primer has a nucleotide sequence selected from SEQ ID NO: 47 or 48, or a fragment thereof comprising at least 20 consecutive nucleotides thereof; and
(b) said reverse primer has a nucleotide sequence selected from SEQ ID NOs: 49-51, or a fragment thereof comprising at least 18 consecutive nucleotides thereof.

24. The method according to claim 1, wherein said forward primer has a nucleotide sequence selected from SEQ ID NO: 47 or 48; and said reverse primer has a nucleotide sequence selected from SEQ ID NOs: 49-51.

25. The method according to claim 1, wherein said at least one amplification product comprises at least one concatemeric amplification product comprising a concatenation of multiple MIRU repeat elements from the same or different MIRU loci, wherein said at least one concatemeric amplification product is greater than 12 Kb by agarose gel electrophoresis, and wherein said detection step comprises detecting said at least one concatemeric amplification product.

26. The method according to claim 25, wherein detecting said at least one concatemeric amplification product comprises the step of digesting said at least one concatemeric amplification product with a restriction endonuclease and detecting the digestion products.

27. The method of claim 1, wherein method steps (a) and (b) are performed using amplification conditions that promote incomplete extension of the forward primer and/or the reverse primer to generate incomplete extension products, wherein said incomplete extension products act as elongated primers in extension step (b), thereby promoting the formation of at least one concatameric amplification product.

28. The method according to claim 1, wherein said forward primer comprises a sequence of at least 3 nucleotides that is complementary to a sequence of at least 3 nucleotides within said reverse primer, such that said forward primer is capable of hybridizing to said reverse primer to form a primer dimer.

29. The method according to claim 28, wherein the 3 nucleotides closest to the 3' terminus of the forward primer are complementary to the 3 nucleotides closest to the 3' terminus of the reverse primer.

30. The method according to claim 28, wherein the method further comprises detecting the presence of primer dimers, and distinguishing said primer dimers from the amplification products.

31. The method of claim 1, wherein the sample is a patient sputum sample, and wherein the method is performed directly on said patient sputum sample without a prior nucleic acid extraction step.

32. The method according to claim 1, wherein said reverse oligonucleotide primer is 19-30 nucleotides long.

33. The method according to claim 1, wherein said forward oligonucleotide primer comprises at least 18 consecutive nucleotides of a nucleotide sequence selected from SEQ ID NOs: 25-39.

34. The method according to claim 1, wherein said reverse oligonucleotide primer comprises at least 19 consecutive nucleotides of the complement of a nucleotide sequence selected from SEQ ID NOs: 40-46.

* * * * *

SEQUENCE LISTING

```
<160> NUMBER OF SEQ ID NOS: 57

<210> SEQ ID NO 1
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: MIRU2 repeat 1

<400> SEQUENCE: 1
aggcgccgct cctcctcatc gcttcgctgt gcatcgtcgc tggcgcgagt ca           52

<210> SEQ ID NO 2
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: MIRU2 repeat 2
```

<400> SEQUENCE: 2
taggcgccgc tcctcctcat cgcttcgctg tgcatcgtcg ccggcgcgag tca            53

<210> SEQ ID NO 3
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: MIRU2 repeat 3

<400> SEQUENCE: 3
taggcgccgc tctcccccgc aagtgggagg tgcccccacc tcatgtgtgg tcaact         56

<210> SEQ ID NO 4
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: MIRU10 repeat 1

<400> SEQUENCE: 4
atggcgccgc tcctcctcat cgctgcgctc tgcatcgtcg ccggcggtag tta            53

<210> SEQ ID NO 5
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: MIRU10 repeat 2, 3 or 4

<400> SEQUENCE: 5
atggcgccgc tcctcctcat cgctgcgctc tgcatcgtcg ccggcggtag tca            53

<210> SEQ ID NO 6
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: MIRU10 repeat 5

<400> SEQUENCE: 6
atggcgccgc tcctcctcat cgctgcgctc tgcatcgtcg ccggcgcggg ggtcat         56

<210> SEQ ID NO 7
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: MIRU16 repeat 1

<400> SEQUENCE: 7
gccgctcctc ctcatcgctt cgctctgcat cgtcgtcggc gcggttca                  48

```
<210> SEQ ID NO 8
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: MIRU16 repeat 2

<400> SEQUENCE: 8
cgagcgccgc tcctcctcat cgcttcgctc tgcatcgtcg tcggcgcggt tca            53

<210> SEQ ID NO 9
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: MIRU16 repeat 3

<400> SEQUENCE: 9
cgagcgccgc tcctcctcat cgcttcgctc tgcatcgtcg tcggcgcggc tcacgtgg      58

<210> SEQ ID NO 10
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: MIRU23 repeat 1

<400> SEQUENCE: 10
tgcgccgctc ctcctcatcg cttcgctctg catcgtcacc ggcgcgactc a              51

<210> SEQ ID NO 11
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: MIRU23 repeat 2

<400> SEQUENCE: 11
tctgcgccgc tcctcctcat cgcttcgctc tgcatcgtca ccggcgcgac tca            53

<210> SEQ ID NO 12
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: MIRU 23 repeat 3 or 4

<400> SEQUENCE: 12
tctgcgccgc tcctgctcat cgcttcgctc tgcatcgtca ccggcgcgac tca            53

<210> SEQ ID NO 13
<211> LENGTH: 58
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: MIRU23 repeat 5

<400> SEQUENCE: 13
tctgcgccgc tcctctcatc gcttcgctct gcatcgtcac cggcgcgcat ggtcagcg      58

<210> SEQ ID NO 14
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: MIRU24 repeat 1

<400> SEQUENCE: 14
cttcgatatg gcgccgctcc tcagcatcgc tgcgctctgc atcgtcgccg gcgc          54

<210> SEQ ID NO 15
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: MIRU26 repeat 1

<400> SEQUENCE: 15
aagcgccgct cctcctcatc gctgcgctct gcatcgtcgc cggcggaggt ca            52

<210> SEQ ID NO 16
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: MIRU26 repeats 2, 3 or 4

<400> SEQUENCE: 16
agcgccgctc ctcctcatcg ctgcgctctg catcgtcgcc ggcggaggtc a             51

<210> SEQ ID NO 17
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: MIRU26 repeat 5

<400> SEQUENCE: 17
gcgccgctcc tcctcatcgc tgcgctctgc atcgtcgccg gcggaggtca caga          54

<210> SEQ ID NO 18
<211> LENGTH: 58
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: MIRU27/ QUB5 repeat 2

<400> SEQUENCE: 18
ctggcgccgc tcctccccat cgctttgctc tgcatcgtcg ccggcgcggg tcactggc        58

<210> SEQ ID NO 19
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: MIRU27/ QUB5 repeat 3

<400> SEQUENCE: 19
ctggcgccgc tcctccccat cgctttgctc tgcatcgtcg ccggcgcggg tca             53

<210> SEQ ID NO 20
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: MIRU27/ QUB5 repeat 4

<400> SEQUENCE: 20
ctggcgccgc tcctccccat cgctttgctc tgcatcgtcg ccggcgcggg tcaatcg         57

<210> SEQ ID NO 21
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: MIRU31/ ETRE repeat 2

<400> SEQUENCE: 21
tctgcgccgc tcctcctcat cgctgcgctc tgcatcgtcg ccggcgccaa cca             53

<210> SEQ ID NO 22
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: MIRY31/ ETRE repeat 3

<400> SEQUENCE: 22
tctgcgccgc tcctcctcat cgctgcgctc tgcatcgtcg ccggcgcgaa gcagcg          56

<210> SEQ ID NO 23
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: MIRU39 repeat 1

<400> SEQUENCE: 23
gcgccgctcc tcctcatcgc tgcgctttgc atcgtcgccg gcgcgggccg        50

<210> SEQ ID NO 24
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: MIRU39 repeat 2

<400> SEQUENCE: 24
ttggcgccgc tcctcctcat cgctgcgctt tgcatcgtcg ccggcgcggg tca        53

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence for forward primer

<400> SEQUENCE: 25
ggcgccgctc ctcctcatcg ct        22

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence for forward primer

<400> SEQUENCE: 26
ggcgccgctc tcccccgcaa gt        22

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence for forward primer

<400> SEQUENCE: 27
ggcgccgctc ctcctcatcg ct        22

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence for forward primer

<400> SEQUENCE: 28
gccgctcctc ctcatcgct        19

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence for forward primer

<400> SEQUENCE: 29
agcgccgctc ctcctcatcg ct                                              22

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence for forward primer

<400> SEQUENCE: 30
tgcgccgctc ctcctcatcg ct                                              22

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence for forward primer

<400> SEQUENCE: 31
tgcgccgctc ctgctcatcg ct                                              22

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence for forward primer

<400> SEQUENCE: 32
tgcgccgctc ctctcatcgc t                                               21

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence for forward primer

<400> SEQUENCE: 33
ggcgccgctc ctcagcatcg ct                                              22

<210> SEQ ID NO 34
<211> LENGTH: 22
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence for forward primer

<400> SEQUENCE: 34
agcgccgctc ctcctcatcg ct                                              22

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence for forward primer

<400> SEQUENCE: 35
gcgccgctcc tcctcatcgc t                                               21

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence for forward primer

<400> SEQUENCE: 36
ggcgccgctc ctccccatcg ct                                              22

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence for forward primer

<400> SEQUENCE: 37
tgcgccgctc ctcctcatcg ct                                              22

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence for forward primer

<400> SEQUENCE: 38
ggcgccgctc ctcctcatcg ct                                              22

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<220> FEATURE:
<223> OTHER INFORMATION: Target sequence for forward primer

<400> SEQUENCE: 39
gcgccgctcc tcctcatcgc t                                              21

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence for reverse primer

<400> SEQUENCE: 40
gctgtgcatc gtcgctggcg                                                20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence for reverse primer

<400> SEQUENCE: 41
gctgtgcatc gtcgccggcg                                                20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence for reverse primer

<400> SEQUENCE: 42
gaggtgcccc cacctcatgt                                                20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence for reverse primer

<400> SEQUENCE: 43
gctctgcatc gtcgccggcg                                                20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence for reverse primer

<400> SEQUENCE: 44
```

```
gctctgcatc gtcgtcggcg                                               20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence for reverse primer

<400> SEQUENCE: 45
gctctgcatc gtcaccggcg                                               20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence for reverse primer

<400> SEQUENCE: 46
gctttgcatc gtcgccggcg                                               20

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 47
ggcgccgctc ctcctcatcg ct                                            22

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 48
ggcgccgctc ctccccatcg ct                                            22

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 49
cgccggcgac gatgcagagc                                               20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
```

-continued reverse primer

<400> SEQUENCE: 50
cgccggtgac gatgcagagc								20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 51
cgccggcgac gatgcaaagc								20

<210> SEQ ID NO 52
<211> LENGTH: 10
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 52 ctgcgctctg								10

<210> SEQ ID NO 53
<211> LENGTH: 10
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 53 cttcgctctg								10

<210> SEQ ID NO 54
<211> LENGTH: 10
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 54 cttcgctgtg								10

<210> SEQ ID NO 55
<211> LENGTH: 10
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 55 ctgcgctttg								10

<210> SEQ ID NO 56
<211> LENGTH: 10
<212> TYPE: DNA
<213> ORGANISM: Artificial Sequence
<220> FEATURE:
<223> OTHER INFORMATION: Description of Artificial Sequence: Synthetic
      probe -continued

```
<400> SEQUENCE: 56
gtgggaggtg                                                              10

<210> SEQ ID NO 57
<211> LENGTH: 10
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 57
ctttgctctg                                                              10
```